US012521752B2

(12) United States Patent
Suzuki et al.

(10) Patent No.: US 12,521,752 B2
(45) Date of Patent: Jan. 13, 2026

(54) NOZZLE, ADHESIVE APPLICATION HEAD, ADHESIVE APPLICATION APPARATUS, AND METHOD OF MAKING DIAPER

(71) Applicant: NORDSON CORPORATION, Westlake, OH (US)

(72) Inventors: Kiwamu Suzuki, Tokyo (JP); Masahito Iwasaki, Tokyo (JP)

(73) Assignee: Nordson Corporation, Westlake, OH (US)

( * ) Notice: Subject to any disclaimer, the term of this patent is extended or adjusted under 35 U.S.C. 154(b) by 105 days.

(21) Appl. No.: 18/443,652

(22) Filed: Feb. 16, 2024

(65) Prior Publication Data

US 2024/0189855 A1 Jun. 13, 2024

Related U.S. Application Data

(63) Continuation of application No. 17/914,391, filed as application No. PCT/US2021/024063 on Mar. 25, 2021, now Pat. No. 11,938,510.

(30) Foreign Application Priority Data

Mar. 26, 2020 (JP) ................................ 2020-055229

(51) Int. Cl.
*B05C 5/02* (2006.01)
*A61F 13/15* (2006.01)

(52) U.S. Cl.
CPC .......... *B05C 5/0275* (2013.01); *B05C 5/0241* (2013.01); *A61F 13/15617* (2013.01)

(58) Field of Classification Search
CPC .................................................... B05C 5/0275
See application file for complete search history.

(56) References Cited

U.S. PATENT DOCUMENTS 4,371,571 A 2/1983 Mcintyre et al.
4,535,919 A * 8/1985 Jameson ................ B05B 7/262 137/538

(Continued)

FOREIGN PATENT DOCUMENTS

CN 1658980 A 8/2005
CN 101209437 A 7/2008

(Continued)

OTHER PUBLICATIONS

Machine translation DE2945297C2 (Year: 1988).*

(Continued)

*Primary Examiner* — Abbas Rashid
*Assistant Examiner* — Wayne K. Swier
(74) *Attorney, Agent, or Firm* — BakerHostetler

(57) ABSTRACT

To improve distribution of adhesive and gas. A nozzle (1) includes a pattern shim (13) having a plurality of first slits (23) and a plurality of second slits (24), an adhesive shim (12) having a plurality of first holes (33), a gas shim (14), a head body (11) having an adhesive outlet (52) and an adhesive distribution groove (51) communicating with the adhesive outlet, and a face plate (15). Adhesive ejection ports are formed at openings of the plurality of first slits, and gas discharge ports are formed at openings of a plurality of second slits in such a manner that the gas discharge ports are located on both sides of each of the adhesive ejection ports. The plurality of first holes (33) communicate with the adhesive distribution groove (51). The plurality of first holes (33) are formed in such a manner that distances of the first holes (33) from the corresponding discharge ejection ports (6) become shorter as distances of the corresponding first holes from the adhesive outlet (52) become longer.

19 Claims, 15 Drawing Sheets

(56) References Cited

U.S. PATENT DOCUMENTS

| | | | | |
|---|---|---|---|---|
| 4,768,718 | A * | 9/1988 | Faulkner, III | B05B 7/0433 239/533.1 |
| 4,774,109 | A | 9/1988 | Hadzimihalis et al. | |
| 4,815,660 | A * | 3/1989 | Boger | B05B 7/10 118/302 |
| 4,844,004 | A | 7/1989 | Hadzimihalis et al. | |
| 4,960,619 | A | 10/1990 | Slautterback et al. | |
| 5,167,712 | A | 12/1992 | Shibata et al. | |
| 5,173,119 | A | 12/1992 | Watanabe et al. | |
| 5,271,794 | A | 12/1993 | Jarrell et al. | |
| 5,294,459 | A | 3/1994 | Hogan et al. | |
| 5,335,825 | A | 8/1994 | Fort | |
| 5,336,322 | A | 8/1994 | Tobisawa et al. | |
| 5,354,378 | A | 10/1994 | Hauser et al. | |
| 5,376,178 | A | 12/1994 | Sato | |
| 5,409,733 | A | 4/1995 | Boger et al. | |
| 5,418,009 | A | 5/1995 | Raterman et al. | |
| 5,421,921 | A | 6/1995 | Gill et al. | |
| 5,423,935 | A | 6/1995 | Benecke et al. | |
| 5,429,840 | A | 7/1995 | Raterman et al. | |
| 5,435,847 | A | 7/1995 | Shibata et al. | |
| 5,458,291 | A | 10/1995 | Brusko et al. | |
| 5,520,735 | A | 5/1996 | Mulder | |
| 5,524,828 | A | 6/1996 | Raterman et al. | |
| 5,540,774 | A | 7/1996 | Smitherman | |
| 5,622,315 | A | 4/1997 | Keane et al. | |
| 5,636,790 | A | 6/1997 | Brusko et al. | |
| 5,639,305 | A | 6/1997 | Brown et al. | |
| 5,700,322 | A * | 12/1997 | Fort | B05B 7/0861 118/313 |
| 5,720,820 | A | 2/1998 | Boger et al. | |
| 5,871,585 | A | 2/1999 | Most et al. | |
| 5,902,540 | A | 5/1999 | Kwok | |
| 6,074,597 | A | 6/2000 | Kwok et al. | |
| 6,077,375 | A | 6/2000 | Kwok | |
| 6,200,635 | B1 | 3/2001 | Kwok | |
| 6,419,344 | B2 | 7/2002 | Fujii et al. | |
| 6,461,430 | B1 | 10/2002 | Kwok | |
| 6,569,244 | B1 | 5/2003 | Jenkins | |
| 6,850,409 | B1 | 2/2005 | Triebes et al. | |
| D550,261 | S | 9/2007 | Bondeson et al. | |
| D588,617 | S | 3/2009 | Burmester et al. | |
| 7,615,175 | B2 | 11/2009 | Nelson et al. | |
| 8,092,207 | B2 | 1/2012 | Cloeren | |
| 8,117,983 | B2 | 2/2012 | Fork et al. | |
| 8,171,973 | B2 | 5/2012 | Ganzer et al. | |
| 8,178,166 | B2 | 5/2012 | Tokimasa et al. | |
| 8,226,391 | B2 | 7/2012 | Fork et al. | |
| 8,387,554 | B2 | 3/2013 | Shibata et al. | |
| 8,399,053 | B2 | 3/2013 | Bondeson et al. | |
| 8,435,600 | B2 | 5/2013 | Burmester et al. | |
| 8,535,756 | B2 | 9/2013 | Bondeson et al. | |
| 8,677,927 | B2 | 3/2014 | Yang | |
| 8,677,928 | B2 | 3/2014 | Kufner et al. | |
| 8,881,674 | B2 | 11/2014 | Somada et al. | |
| 8,979,521 | B2 | 3/2015 | Kondo | |
| 9,061,311 | B2 | 6/2015 | Tsuchida et al. | |
| 9,186,693 | B2 | 11/2015 | Ukegawa | |
| 9,327,429 | B2 | 5/2016 | Ausen et al. | |
| 9,337,471 | B2 | 5/2016 | Cobb | |
| 9,415,590 | B2 | 8/2016 | Barton et al. | |
| 9,492,836 | B2 | 11/2016 | Wang et al. | |
| 9,539,606 | B2 | 1/2017 | Park et al. | |
| 9,731,316 | B2 | 8/2017 | Ukegawa | |
| 9,855,583 | B2 * | 1/2018 | Crane | B05D 5/00 |
| 10,137,472 | B2 | 11/2018 | Ayers | |
| 10,421,227 | B2 | 9/2019 | Kalish et al. | |
| 10,478,347 | B2 | 11/2019 | Eimann et al. | |
| 10,493,485 | B2 | 12/2019 | Hirai | |
| 10,500,606 | B2 | 12/2019 | Ikagawa | |
| 10,525,498 | B2 | 1/2020 | Jung et al. | |
| 10,675,654 | B2 | 6/2020 | Kuenne | |
| 11,148,167 | B2 | 10/2021 | Saine | |
| 11,583,887 | B2 | 2/2023 | Burmester et al. | |
| 11,607,706 | B2 | 3/2023 | Saine | |
| 11,684,947 | B2 | 6/2023 | Graff | |
| 11,766,694 | B2 | 9/2023 | Saine | |
| 11,938,510 | B2 | 3/2024 | Suzuki et al. | |
| 11,975,350 | B2 | 5/2024 | Saine | |
| 12,296,356 | B2 | 5/2025 | Suzuki et al. | |
| 2001/0002281 | A1 | 5/2001 | Mandai et al. | |
| 2002/0018856 | A1 | 2/2002 | Kufner et al. | |
| 2002/0036050 | A1 | 3/2002 | Kwok | |
| 2005/0205689 | A1 | 9/2005 | Crane et al. | |
| 2007/0204793 | A1 | 9/2007 | Kufner et al. | |
| 2008/0145530 | A1 | 6/2008 | Bondeson et al. | |
| 2009/0022890 | A1 | 1/2009 | Takahashi et al. | |
| 2009/0258138 | A1 | 10/2009 | Burmester et al. | |
| 2010/0117254 | A1 | 5/2010 | Fork et al. | |
| 2011/0073035 | A1 | 3/2011 | Horikawa | |
| 2012/0263906 | A1 | 10/2012 | Ausen et al. | |
| 2013/0004729 | A1 | 1/2013 | Ausen et al. | |
| 2013/0011600 | A1 | 1/2013 | Ausen et al. | |
| 2013/0129915 | A1 | 5/2013 | Shibata et al. | |
| 2013/0192520 | A1 | 8/2013 | Burmester et al. | |
| 2013/0240122 | A1 | 9/2013 | Adams | |
| 2014/0261967 | A1 * | 9/2014 | Li | B05C 5/0241 156/78 |
| 2015/0202648 | A1 | 7/2015 | Bolyard, Jr. | |
| 2016/0243745 | A1 | 8/2016 | Iuliano et al. | |
| 2017/0014853 | A1 | 1/2017 | Lessley et al. | |
| 2017/0197347 | A1 | 7/2017 | Ausen et al. | |
| 2017/0304863 | A1 | 10/2017 | Bolyard, Jr. | |
| 2019/0118449 | A1 | 4/2019 | Greenlund et al. | |
| 2019/0283072 | A1 * | 9/2019 | Woodlief | B29B 13/022 |
| 2023/0140800 | A1 | 5/2023 | Lee et al. | |

FOREIGN PATENT DOCUMENTS

| | | | | |
|---|---|---|---|---|
| CN | 101733231 | A | 6/2010 | |
| CN | 102029242 | A | 4/2011 | |
| DE | 2945297 | C2 * | 6/1988 | B27G 11/00 |
| JP | 10-183454 | A | 7/1998 | |
| JP | 11-333373 | A | 12/1999 | |
| JP | 2000-070832 | A | 3/2000 | |
| JP | 2003-071328 | A | 3/2003 | |
| JP | 2008-104998 | A | 5/2008 | |
| JP | 2008-212919 | A | 9/2008 | |
| JP | 2009-291780 | A | 12/2009 | |
| JP | 2011-147939 | A | 8/2011 | |
| JP | 2017-504473 | A | 2/2017 | |
| WO | 2019/168875 | A1 | 9/2019 | |
| WO | 2019/239569 | A1 | 12/2019 | |

OTHER PUBLICATIONS

Machine translation CN101733231A (Year: 2010).*
Machine translation JP2011147939A (Year: 2011).*
IPEA/409—International Preliminary Report on Patentability Mailed on Oct. 6, 2022 for WO Application No. PCT/US21/024063.
ISA/220—Notification of Transmittal or Search Report and Written Opinion of the ISA, or the Declaration Mailed on Jul. 9, 2021 for WO Application No. PCT/US21/024063.

* cited by examiner (a)

(b)

(a)
1
17
54
12
13
11
14
53
15
52
51
33
23
6
2
(b)
1
58
55
154
12
13
11
14
35
151
25
15
45
24
152
7
153
2
43

(a)

(b)

(a)

(b)

NOZZLE, ADHESIVE APPLICATION HEAD, ADHESIVE APPLICATION APPARATUS, AND METHOD OF MAKING DIAPER

CROSS REFERENCE TO RELATED APPLICATIONS

This application is a continuation application of U.S. patent application Ser. No. 17/914,391, filed Sep. 26, 2022, which claims priority to National Stage Application of International Patent Application No. PCT/US2021/024063, filed Mar. 25, 2021, which claims the benefit of Japanese Patent Application No. 2020-055229, filed Mar. 26, 2020, the entirety of each of which is incorporated herein for any and all purposes.

TECHNICAL FIELD

The present invention relates to a nozzle, an adhesive application head, an adhesive application apparatus, and a method of making a diaper.

BACKGROUND

Hitherto, there exists a nozzle configured to eject a liquid in a fibrous shape and cause gas streams to impinge on the fibrous liquid substantially from both sides to oscillate the liquid to thereby form an omega-shaped pattern (PATENT LITERATURE 1). Further, there exists a nozzle configured to oscillate a fibrous adhesive to apply the fibrous adhesive on a cord-like member so as to bond the cord-like member to a substrate (PATENT LITERATURE 2, PATENT LITERATURE 3).

Still further, there exists a nozzle having a pair of gas holes formed at symmetric positions with respect to an adhesive ejection port. When the nozzle is mounted to an application apparatus, the adhesive ejection port extends in a predetermined direction and is inclined at a predetermined angle with respect to a relative moving direction between the nozzle and a substrate (PATENT LITERATURE 4). Gas streams are jetted to fibers of a viscous fluid material ejected from the nozzle to vibrate the viscous fluid material in the predetermined direction.

Still further, there exists an adhesive application head having an adhesive nozzle and gas discharge ports, which are formed by laminating a plurality of plates. The gas discharge ports, which are each inclined at a predetermined angle, are formed on both sides of the adhesive nozzle (PATENT LITERATURE 5). Specifically, the adhesive nozzle configured to eject an adhesive is formed with a central convex portion of a central plate and convex portions of both end plates, which sandwich the central convex portion therebetween. A gas jetted from each of openings of slits on the both sides of the adhesive nozzle is guided toward the adhesive being ejected. In the adhesive application head described in PATENT LITERATURE 5, the central plate has a plurality of first convex portions arranged side by side at an outer edge, a plurality of first slits formed in such a manner as to correspond to the plurality of first convex portions, and a plurality of pairs of second slits formed in such a manner as to correspond to the plurality of first convex portions. Each of the pair of end plates has a plurality of second convex portions formed in such a manner as to correspond to the plurality of first convex portions. Specifically, a plurality of adhesive ejection ports are formed by one set of superposed plates.

PRIOR ART DOCUMENTS AND PATENT LITERATURE

PATENT LITERATURE 1: Japanese Patent Application Laid-Open No. 2000-070832
PATENT LITERATURE 2: Japanese Patent Application Laid-Open No. 2003-071328
PATENT LITERATURE 3: Japanese Patent Application Laid-Open No. H11-333373
PATENT LITERATURE 4: Japanese Patent Application Laid-Open No. 2008-104998
PATENT LITERATURE 5: Japanese Patent Application Laid-Open No. 2011-147939

SUMMARY

Problems to be Solved by the Invention

In the configuration in which the plurality of adhesive ejection ports are formed by the one set of superposed plates, flow rates of adhesive streams supplied to the plurality of adhesive ejection ports and flow rates of air streams supplied to the plurality of gas discharge ports are different in a center portion and end portions of the plates. As a result, ejection amounts of adhesive ejected from the plurality of adhesive ejection ports, amplitudes of patterns of the adhesive streams, and amplitude cycles (frequencies) become non-uniform over the plurality of adhesive ejection ports, and hence adhesive fibers having the same fiber diameter cannot come into contact with rubber threads in the same cycles. Thus, bonding strength varies among the rubber threads, and there arises a problem in that an ideal application state cannot be obtained.

Further, in order to increase a production rate of items (such as infant paper diapers, adult paper diapers, and feminine hygiene items), the rubber thread, which is a material for the items, is required to be transported at high speed in accordance with the production rate. However, when the adhesive is applied at a substantially right angle with respect to a moving direction of the rubber thread as in the related art, the ejected adhesive is more liable to be repelled by a surface of the rubber thread and scattered to the surroundings as the moving speed of the rubber thread increases. As a result, the adhesive may fail to adhere to a desired portion of the rubber thread to cause a bonding defect, or scattered adhesive fibers may contaminate peripheral devices. In order to avoid the above-mentioned problems, the production rate is decreased to such a rate at which the scattering of the adhesive does not occur, or an ejection speed, specifically, an ejection amount of the adhesive is increased, to thereby prevent the adhesive from being repelled by the rubber thread moving at high speed. However, there arises a problem in that production conditions are restricted.

Thus, the present invention has an object to provide a nozzle that enables improvement of uniformity in distribution of an adhesive to be distributed to a plurality of adhesive ejection ports and uniformity in distribution of a gas to be distributed to a plurality of gas discharge ports and enables suppression of repelling and scattering of the adhesive by a rubber thread.

Solutions for Solving the Problems

In order to solve the above-mentioned problems, according to one embodiment of the present invention, there is provided a nozzle, including:

a pattern shim having a plurality of tapered first convex portions protruding from an outer edge outwardly, a plurality of first slits which are open at tips of the plurality of first convex portions, respectively, a plurality of second slits provided on both sides of each of the plurality of first slits and are open at portions adjacent to a corresponding first convex portion, and a first gas hole;

an adhesive shim having a plurality of tapered second convex portions protruding from an outer edge outwardly and having a shape wider than the first convex portions, a plurality of first holes as adhesive flow paths, and a second gas hole;

a gas shim having a plurality of tapered third convex portions protruding from an outer edge outwardly and having a shape wider than the first convex portions, a plurality of second holes as gas flow paths, and a third gas hole;

a head body having an adhesive inlet, an adhesive outlet, an adhesive flow path connecting the adhesive inlet and the adhesive outlet, an adhesive distribution groove communicating with the adhesive outlet, a gas inlet, a gas outlet, and a gas flow path connecting the gas inlet and the gas outlet;

a face plate having a first gas distribution groove, a second gas distribution groove communicating with the first gas distribution groove, and a third gas distribution groove communicating with the second gas distribution groove; and fixing means for fixing the head body, the adhesive shim, the pattern shim, the gas shim, and the face plate arranged in order of mention so that the adhesive distribution groove communicates with the plurality of first holes, the plurality of first holes communicate with the plurality of first slits, the gas outlet communicates with the first gas hole, the first gas hole communicates the second gas hole, the second gas hole communicates with the third gas hole, the third gas hole communicates with the first gas distribution groove, the third gas distribution groove communicates with the plurality of second holes, and the plurality of second holes communicates with the plurality of second slits, wherein the plurality of first convex portions are sandwiched by the plurality of second convex portions and the plurality of third convex portions to form adhesive discharge ports at openings of the plurality of first slits and to form gas discharge ports, at openings of the plurality of second slits, provided on both sides of each of the adhesive discharge ports, and wherein the plurality of first holes are configured so that a distance from an adhesive ejection port becomes shorter as a distance from the adhesive outlet becomes longer.

Effects of the Invention

According to the present invention, uniformity in distribution of the adhesive to be distributed to the plurality of adhesive ejection ports and uniformity in distribution of the gas to be distributed to the plurality of gas discharge ports can be improved.

According to an aspect of this disclosure, a nozzle may comprise:

a pattern shim having a plurality of tapered first convex portions protruding from an outer edge outwardly; a plurality of first slits which open at tips of the plurality of first convex portions, respectively; a plurality of second slits provided on both sides of each of the plurality of first slits and open at portions adjacent to a corresponding first convex portion; and a first gas hole;

an adhesive shim having a plurality of tapered second convex portions protruding from an outer edge outwardly and having a shape wider than the first convex portions; a plurality of first holes as adhesive flow paths; and a second gas hole;

a gas shim having a plurality of tapered third convex portions protruding from an outer edge outwardly and having a shape wider than the first convex portions; a plurality of second holes as gas flow paths; and a third gas hole;

a head body having an adhesive inlet, an adhesive outlet, an adhesive flow path connecting the adhesive inlet and the adhesive outlet, an adhesive distribution groove communicating with the adhesive outlet, a gas inlet, a gas outlet, and a gas flow path connecting the gas inlet and the gas outlet;

a face plate having a first gas distribution groove, a second gas distribution groove communicating with the first gas distribution groove, and a third gas distribution groove communicating with the second gas distribution groove; and a fixing means for fixing the head body, the adhesive shim, the pattern shim, the gas shim, and the face plate arranged in order of mention so that the adhesive distribution groove communicates with the plurality of first holes, the plurality of first holes communicate with the plurality of first slits, the gas outlet communicates with the first gas hole, the first gas hole communicates the second gas hole, the second gas hole communicates with the third gas hole, the third gas hole communicates with the first gas distribution groove, the third gas distribution groove communicates with the plurality of second holes, and the plurality of second holes communicates with the plurality of second slits, wherein the plurality of first convex portions are sandwiched by the plurality of second convex portions and the plurality of third convex portions to form adhesive discharge ports at openings of the plurality of first slits and to form gas discharge ports, at openings of the plurality of second slits, provided on both sides of each of the adhesive discharge ports, and wherein the plurality of first holes are configured so that a distance from an adhesive discharge port becomes shorter as a distance from the adhesive outlet becomes longer.

Optionally, adhesive discharged from the adhesive discharge ports may be applied on objects moving in a moving direction with respect to the adhesive discharge ports.

Optionally, the head body has an inclined surface which is inclined with respect to the moving direction; the adhesive distribution groove and the gas outlet are formed in the inclined surface; the adhesive shim is disposed in contact with the inclined surface; axes passing through the adhesive discharge ports of the plurality of first slits extend along the inclined surface to form an acute angle with respect to the moving direction; and axes passing through the gas discharge ports of the plurality of second slits extend along the inclined surface to form an acute angle with respect to the moving direction.

Optionally, the face plate has a plurality of guide grooves, and wherein each of the guide grooves is positioned in a vicinity of a corresponding adhesive discharge port and has a concave surface configured to receive the object and guide the object along the moving direction.

Optionally, gases are discharged from the gas discharge ports formed on both sides of the corresponding adhesive discharge port in symmetry with respect to and toward the adhesive discharged from the corresponding adhesive discharge port so that the gases discharged from the gas discharge ports impinge on the adhesive discharged from the corresponding adhesive discharge port at a same distance from the corresponding adhesive discharge port, and wherein the plurality of second convex portions and the plurality of third convex portions are disposed so as to cover the gas discharge ports as viewed along the moving direction.

Optionally, the plurality of first holes are located on intersecting points of the plurality of first slits with a line forming a predetermined angle with a line extending along a width direction of the adhesive shim.

Optionally, the plurality of first holes are long holes elongated in a direction the plurality of first slits extend.

Optionally, lengths of the long holes are set so as to become longer in accordance with the distance from the adhesive outlet.

Optionally, the plurality of first holes are round-holes, and wherein diameters of the round-holes are set so as to become larger in accordance with the distance from the adhesive outlet.

Optionally, the plurality of first holes are round-holes, and wherein diameters of the round-holes are the same.

Optionally, the third gas distribution groove is longer than the first gas distribution groove in a width direction of the face plate, wherein a depth of the second gas distribution groove is shallower than a depth of the first gas distribution groove and a depth of the third gas distribution groove, and wherein a width of the second gas distribution groove is widened in the width direction of the face plate as going from the first gas distribution groove to the third gas distribution groove.

Optionally, the face plate has a pair of positioning pins, wherein the pattern shim has a positioning hole through which one of the pair of positioning pins passes, and a positioning groove provided on a part of an outer periphery of the pattern shim and engaging with the other of the pair of positioning pins, wherein the adhesive shim has a positioning hole through which the one of the pair of positioning pins passes, and a positioning groove provided on a part of an outer periphery of the adhesive shim and engaging with the other of the pair of positioning pins, and wherein the gas shim has a positioning hole through which the one of the pair of positioning pins passes, and a positioning groove provided on a part of an outer periphery of the gas shim and engaging with the other of the pair of positioning pins.

According to some embodiments, an adhesive application head may comprise a nozzle as recited in any one or more of the embodiments or combinations of embodiments above; and a dispenser valve, to which the nozzle is mounted, configured to supply an adhesive to the nozzle.

According to another embodiment, an adhesive application apparatus may comprise:

- a transport roller for transporting an object to an application position in a moving direction;
- a melter for supplying an adhesive;
- a pump for pumping the adhesive from the melter;
- a hose through which the adhesive pumped by the pump passes;
- a manifold for distribute the adhesive supplied from the hose;
- a first regulator for depressurizing a compression gas;
- a solenoid valve for supplying the compression gas depressurized by the first regulator in accordance with an external signal;
- a dispenser valve, to which the adhesive is distributed from the manifold, which opens and closes an adhesive discharge port by the compression gas supplied from the solenoid valve, and discharges the adhesive for the adhesive discharge port;
- a second regulator for depressurizing a compression gas; and
- a nozzle for discharge the adhesive supplied from the dispenser valve and impinging the compression gas depressurized by the second regulator on the adhesive to oscillate the adhesive to apply the adhesive on the object moving in the moving direction, wherein the nozzle comprises:

- a pattern shim having a plurality of tapered first convex portions protruding from an outer edge outwardly, a plurality of first slits which open at tips of the plurality of first convex portions, respectively, a plurality of second slits provided on both sides of each of the plurality of first slits and open at portions adjacent to a corresponding first convex portion, and a first gas hole;
- an adhesive shim having a plurality of tapered second convex portions protruding from an outer edge outwardly and having a shape wider than the first convex portions, a plurality of first holes as adhesive flow paths, and a second gas hole;
- a gas shim having a plurality of tapered third convex portions protruding from an outer edge outwardly and having a shape wider than the first convex portions, a plurality of second holes as gas flow paths, and a third gas hole;
- a head body having an adhesive inlet, an adhesive outlet, an adhesive flow path connecting the adhesive inlet and the adhesive outlet, an adhesive distribution groove communicating with the adhesive outlet, a gas inlet, a gas outlet, and a gas flow path connecting the gas inlet and the gas outlet;
- a face plate having a first gas distribution groove, a second gas distribution groove communicating with the first gas distribution groove, and a third gas distribution groove communicating with the second gas distribution groove; and
- fixing means for fixing the head body, the adhesive shim, the pattern shim, the gas shim, and the face plate arranged in order of mention so that the adhesive distribution groove communicates with the plurality of first holes, the plurality of first holes communicate with the plurality of first slits, the gas outlet communicates with the first gas hole, the first gas hole communicates the second gas hole, the second gas hole communicates with the third gas hole, the third gas hole communicates with the first gas distribution groove, the third gas distribution groove communicates with the plurality of second holes, and the plurality of second holes communicates with the plurality of second slits,
- wherein the plurality of first convex portions are sandwiched by the plurality of second convex portions and the plurality of third convex portions to form adhesive discharge ports at openings of the plurality of first slits and to form gas discharge ports, at openings of the plurality of second slits, provided on both sides of each of the adhesive discharge ports, and wherein the plurality of first holes are configured so that a distance from an adhesive discharge port becomes shorter as a distance from the adhesive outlet becomes longer.

Optionally, the head body has an inclined surface which is inclined with respect to the moving direction, the adhesive distribution groove and the gas outlet are formed in the inclined surface, the adhesive shim is disposed in contact with the inclined surface, axes passing through the adhesive discharge ports of the plurality of first slits extend along the inclined surface to form an acute angle with respect to the moving direction, and axes passing through the gas discharge ports of the plurality of second slits extend along the inclined surface to form an acute angle with respect to the moving direction.

Optionally, the face plate has a plurality of guide grooves, and wherein each of the guide grooves is positioned in a vicinity of a corresponding adhesive discharge port and has a concave surface configured to receive the object and guide the object along the moving direction.

Optionally, gases are discharged from the gas discharge ports formed on both sides of the corresponding adhesive discharge port in symmetry with respect to and toward the adhesive discharged from the corresponding adhesive discharge port so that the gases discharged from the gas discharge ports impinge on the adhesive discharged from the corresponding adhesive discharge port at a same distance from the corresponding adhesive discharge port, and wherein the plurality of second convex portions and the plurality of third convex portions are disposed so as to cover the gas discharge ports as viewed along the moving direction.

Optionally, the plurality of first holes are located on intersecting points of the plurality of first slits with a line forming a predetermined angle with a line extending along a width direction of the adhesive shim.

Optionally, the plurality of first holes are long holes elongated in a direction the plurality of first slits extend.

Optionally, lengths of the long holes are set so as to become longer in accordance with the distance from the adhesive outlet.

Optionally, the plurality of first holes are round-holes, and wherein diameters of the round-holes are set so as to become larger in accordance with the distance from the adhesive outlet.

Optionally, the plurality of first holes are round-holes, and wherein diameters of the round-holes are the same.

Optionally, the third gas distribution groove is longer than the first gas distribution groove in a width direction of the face plate, wherein a depth of the second gas distribution groove is shallower than a depth of the first gas distribution groove and a depth of the third gas distribution groove, and wherein a width of the second gas distribution groove is widened in the width direction of the face plate as going from the first gas distribution groove to the third gas distribution groove.

Optionally, the face plate has a pair of positioning pins, wherein the pattern shim has a positioning hole through which one of the pair of positioning pins passes, and a positioning groove provided on a part of an outer periphery of the pattern shim and engaging with the other of the pair of positioning pins, wherein the adhesive shim has a positioning hole through which the one of the pair of positioning pins passes, and a positioning groove provided on a part of an outer periphery of the adhesive shim and engaging with the other of the pair of positioning pins, and wherein the gas shim has a positioning hole through which the one of the pair of positioning pins passes, and a positioning groove provided on a part of an outer periphery of the gas shim and engaging with the other of the pair of positioning pins.

According to another embodiment, a method of making a diaper may comprise:

moving a plurality of rubber threads;

applying a plurality of hot melt adhesive fibers discharged from a nozzle as recited in any one or combination of examples listed above on the plurality of rubber threads, respectively, in a wave pattern formed by impinging gas on the plurality of hot melt adhesive fibers, and sandwiching the plurality of rubber threads on which the plurality of hot melt adhesive fibers are applied, respectively, by two substrates.

DETAILED DESCRIPTION OF ILLUSTRATIVE EMBODIMENTS

The disclosed invention will be described based on various envisioned and preferred embodiments with reference to the accompanying drawings. Note that, in the following description of the embodiment, sizes, materials, shapes, positional relationship, etc. of components are not intended to limit the scope of the present invention exclusively thereto unless otherwise specified.

Adhesive Application Apparatus

Figure 1:
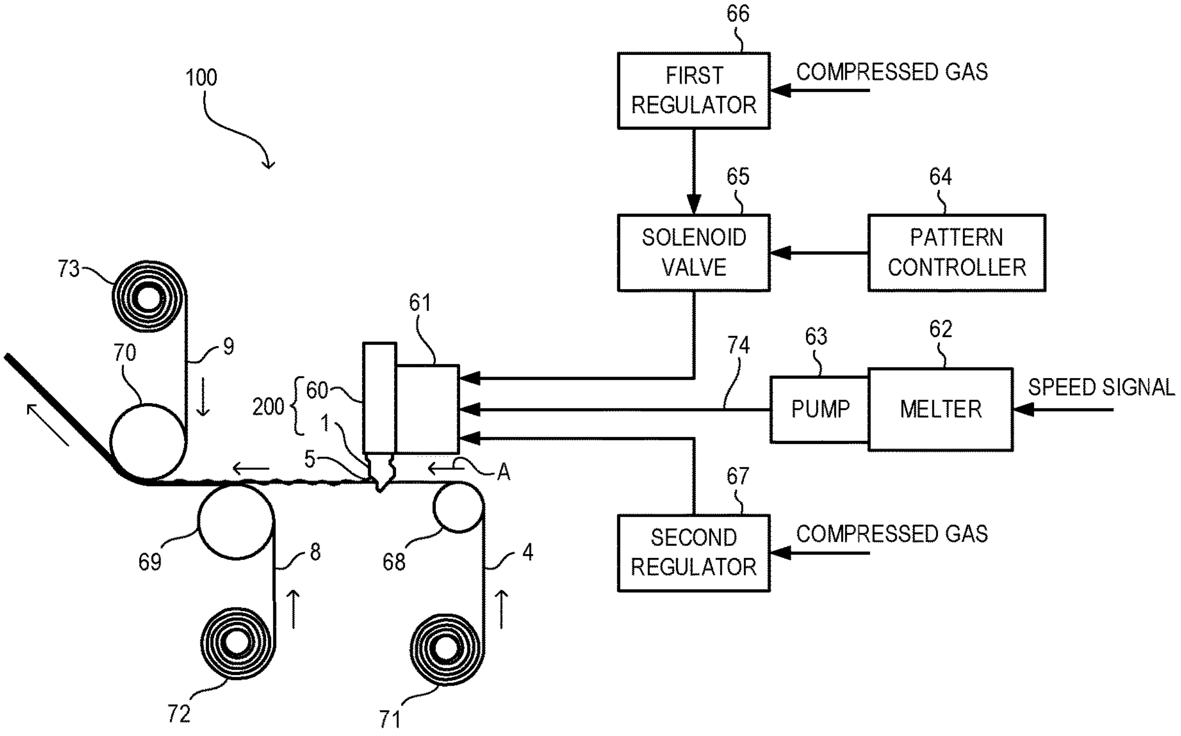
FIG. 1 is a block diagram of an adhesive application apparatus.

An overall structure of an adhesive application apparatus 100 is described with reference to FIG. 1. The adhesive application apparatus 100 can be used to make disposal hygiene items such as infant paper diapers, adult paper diapers, and feminine hygiene items. FIG. 1 is a block diagram of the adhesive application apparatus 100. The adhesive application apparatus 100 includes a nozzle 1, a dispenser valve 60, a manifold 61, a melter 62, a pump 63, a pattern controller 64, a solenoid valve 65, a first regulator 66, and a second regulator 67. An adhesive application head 200 includes the dispenser valve 60 and the nozzle 1 mounted to the dispenser valve 60. The adhesive application apparatus 100 further includes a guide roller (transport roller) 68, a first transport roller 69, and a second transport roller 70.

A hot melt adhesive (hereinafter referred to simply as "adhesive") 5 is melted by the melter 62, and is stored in a tank inside the melter 62. The adhesive 5 is pumped by the pump 63 from the melter 62 through a heating hose 74 to the manifold 61. The melter 62 receives a speed signal corresponding to a moving speed (transporting speed) of rubber threads 4 from a base unit, and controls the amount of the adhesive 5 to be supplied by the pump 63 in accordance with the speed signal. When a production rate is increased, the amount of the adhesive 5 supplied from the melter 62 is increased in accordance with the speed signal from the base unit. When the production rate is decreased, the amount of the adhesive 5 supplied from the melter 62 is reduced in accordance with the speed signal from the base unit.

Figure 2:
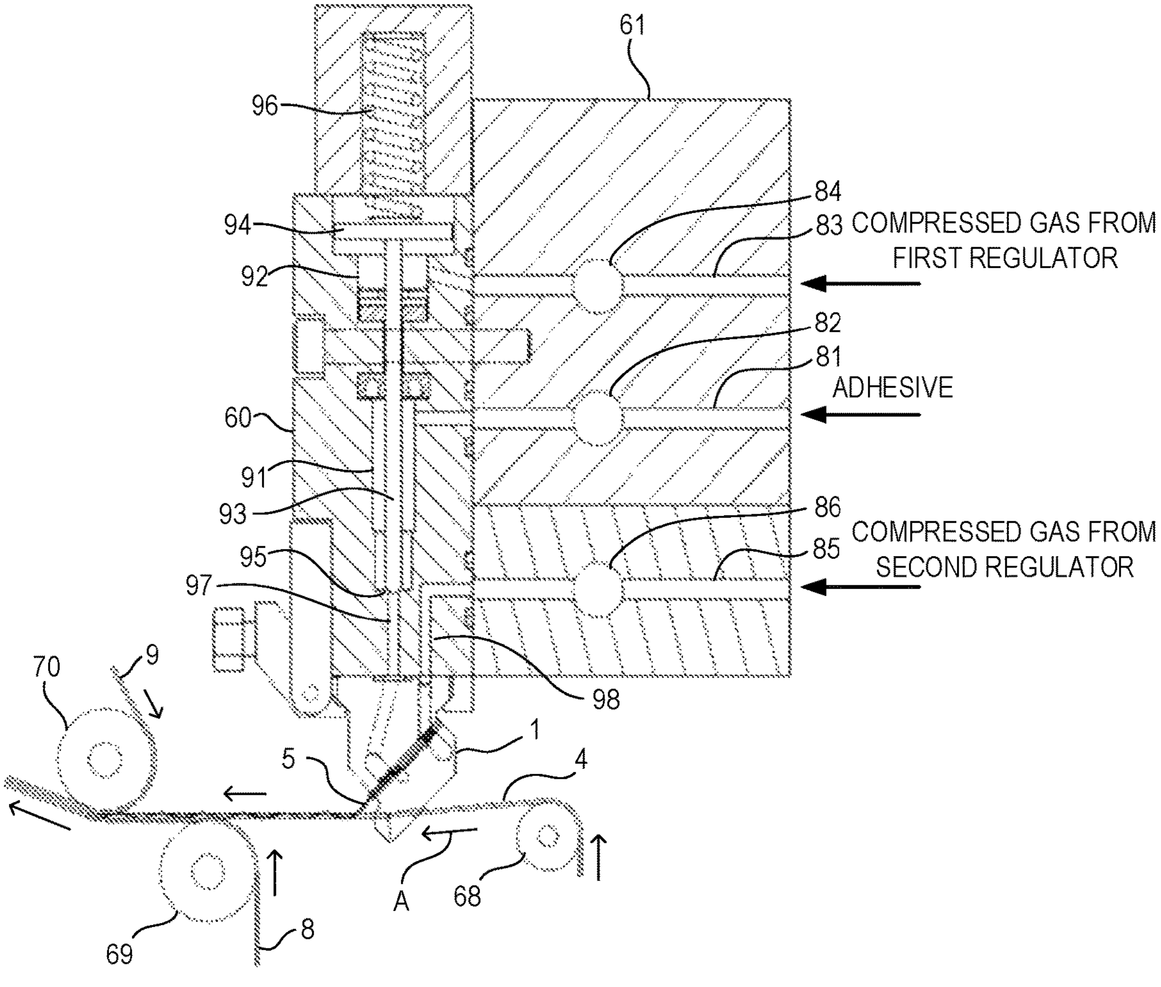
FIG. 2 is a sectional view of a nozzle, a dispenser valve, and a manifold.

FIG. 2 is a sectional view of the nozzle 1, the dispenser valve 60, and the manifold 61. The adhesive 5 is supplied to an adhesive passage 81 formed in the manifold 61. A plurality of dispenser valves 60 can be mounted to the manifold 61. The adhesive 5 passes from the adhesive passage 81 through a common adhesive passage 82 to be distributed into the dispenser valves 60. The adhesive 5 is supplied to a valve chamber 91 formed in the dispenser valve 60. The dispenser valve 60 has a piston chamber 92. The dispenser valve 60 includes a valve rod 93 that extends through the valve chamber 91 and the piston chamber 92. The valve rod 93 is movably provided in the dispenser valve 60.

A piston 94 provided in the piston chamber 92 is mounted to an end portion of the valve rod 93. The piston 94 is urged by a spring 96 so that a tip portion of the valve rod 93 comes into contact with an adhesive discharge port 95. The adhesive discharge port 95 communicates with the nozzle 1 through intermediation of an adhesive discharge passage 97.

As illustrated in FIG. 1, a compression gas is depressurized by the first regulator 66, and is then supplied to the solenoid valve 65. In this embodiment, the compression gas is compression air. However, the compression gas may be a compressed inert gas. The first regulator 66 is configured to maintain a pressure of the compression gas at a predetermined pressure. The pattern controller 64 is configured to control opening and closing of the solenoid valve 65 in accordance with an application pattern of the adhesive. When the solenoid valve 65 is opened, the compression gas is supplied to a first gas passage 83 of the manifold 61 illustrated in FIG. 2. The compression gas passes from the first gas passage 83 through a first common gas passage 84 to be distributed to the piston chamber 92 of each of the dispenser valves 60.

The pattern controller 64 is configured to continuously or intermittently open and close the solenoid valve 65 in accordance with the application pattern so as to control timing at which the valve rod 93 of the dispenser valve 60 opens and closes the adhesive discharge port 95. When the solenoid valve 65 is opened in accordance with a signal (external signal) output from the pattern controller 64, the compression gas, which has been depressurized by the first regulator 66, is supplied to the dispenser valve 60 to open the adhesive discharge port 95. As a result, the adhesive 5 is supplied to the nozzle 1, and is ejected therefrom. When the valve rod 93 continuously opens the adhesive discharge port 95, the adhesive 5 is continuously applied to the rubber threads 4. When the valve rod 93 intermittently opens and closes the adhesive discharge port 95, the adhesive 5 is intermittently applied to the rubber threads 4.

As illustrated in FIG. 1, the compression gas is depressurized by the second regulator 67, and is then supplied to the manifold 61. As illustrated in FIG. 2, the compression gas flowing from the second regulator 67 passes from a second gas passage 85 through a second common gas passage 86 to be distributed to a pair of gas discharge passages 98 of each of the dispenser valves 60. The compression gas, which has been depressurized by the second regulator 67, is continuously supplied to the nozzle 1, and is ejected therefrom. The compression gas ejected from the nozzle 1 impinges on the adhesive 5 being ejected in a filament-like shape from the nozzle 1 to oscillate the adhesive 5. The oscillated adhesive 5 is applied on an outer periphery of the rubber threads 4 that are being continuously moved.

Through the regulation of the pressure of the compression gas by the second regulator 67, a width of oscillation of the adhesive 5 can be adjusted. When the pressure of the compression gas after being regulated by the second regulator 67 is high, the width of oscillation of the adhesive 5 is increased. When the pressure of the compression gas after being regulated by the second regulator 67 is low, the width of oscillation of the adhesive 5 is reduced. The second regulator 67 may be an electro-pneumatic regulator. When the electro-pneumatic regulator is controlled in accordance with an electric signal corresponding to the moving speed of the rubber threads 4, the pressure of the compression gas can be set variable. When an ejection amount of the adhesive 5 is increased, the adhesive 5 is less liable to be oscillated. Thus, in this case, the width of oscillation of the adhesive 5 can be kept constant by increasing the pressure of the compression gas supplied from the second regulator 67.

The rubber threads (objects) 4 are wound into a roll 71. The rubber threads 4 are supplied from the roll 71 to the nozzle 1 through intermediation of the guide roller 68. A first substrate (lower substrate) 8 is wound into a roll 72. The first substrate 8 is supplied from the roll 72 to the first transport roller 69 to be bonded to the rubber threads 4 applied with the adhesive 5. A second substrate (upper substrate) 9 is wound into a roll 73. The second substrate 9 is supplied from the roll 73 to the second transport roller 70 to be bonded to the rubber threads 4 applied with the adhesive 5. The first substrate 8 and the second substrate 9 are bonded to each other in such a manner that the rubber threads 4 applied with the adhesive 5 are sandwiched therebetween.

Nozzle

Figure 3:
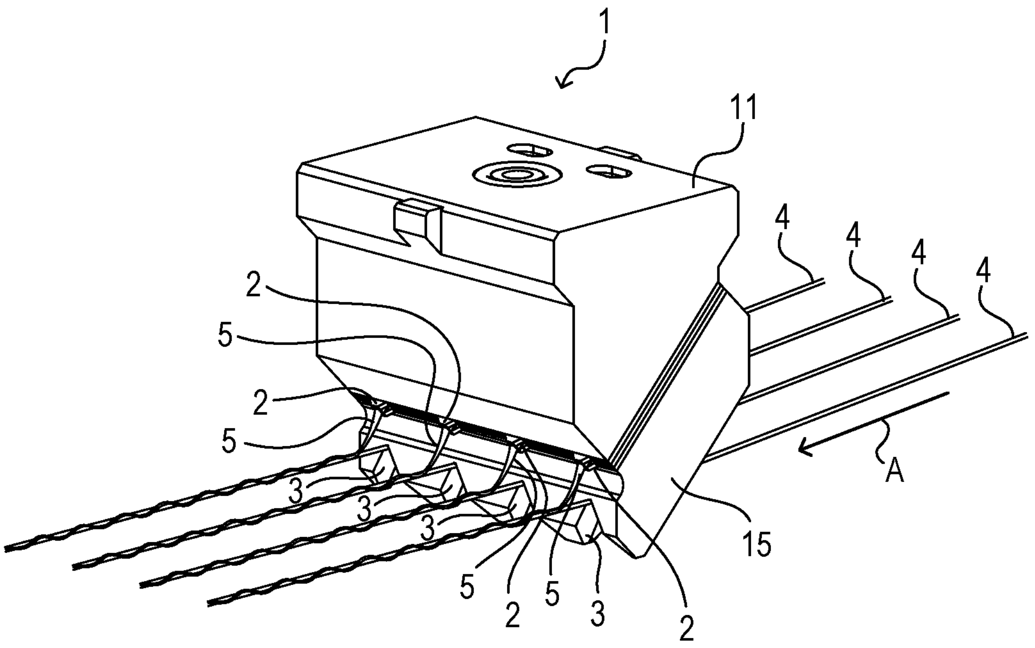
FIG. 3 is a view for illustrating the nozzle.
Figure 3:
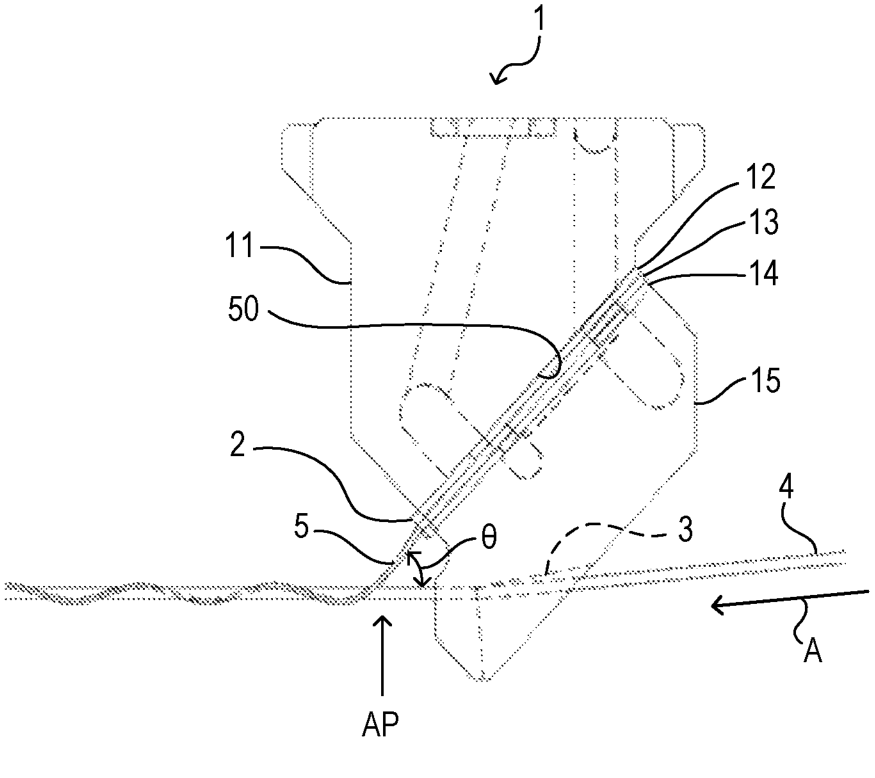

Now, the nozzle 1 is described. FIG. 3 is a view for illustrating the nozzle 1. FIG. 3(*a*) is a perspective view of the nozzle 1. FIG. 3(*b*) is a side view of the nozzle 1. The nozzle 1 has a plurality of ejection ports 2 and a plurality of guide grooves 3 corresponding to the plurality of ejection ports 2, respectively. In this embodiment, four ejection ports 2 and four guide grooves 3 are formed. However, the number of ejection ports 2 and the number of guide grooves 3 are not each limited to four, and may be two, three, five, or other numbers. It is only required that one nozzle I have at least two ejection ports 2. The guide grooves 3 are configured to guide the rubber threads 4 that are moved along a moving direction (transporting direction) A to positions optimal for the application of the adhesive 5.

Figure 4:
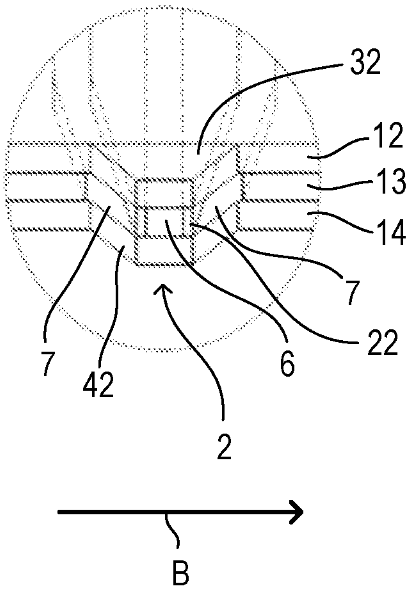
FIG. 4 is an enlarged view of an ejection port.

FIG. 4 is an enlarged view of the ejection port 2. The ejection port 2 includes an adhesive ejection port 6 and gas discharge ports (air discharge ports) 7. The adhesive ejection port 6 is configured to eject the adhesive 5. The gas discharge ports 7 are configured to jet the compression gas. The two gas discharge ports 7 are arranged on both sides of the adhesive ejection port 6 in a width direction B orthogonal to the moving direction A of the rubber threads 4. The nozzle 1 applies the adhesive 5 on each of the rubber threads 4, which are being moved along the moving direction A under a state in which the compression gas is jetted from the gas discharge ports 7 toward the adhesive 5 being ejected from the adhesive ejection port 6 for each of the rubber threads 4. Streams of the compression gas ejected from the gas discharge ports 7 are caused to impinge on the adhesive 5 that is being ejected from the adhesive ejection port 6 in a filament-like shape to thereby oscillate the adhesive 5. The oscillated adhesive 5 is continuously applied on the outer periphery of the rubber thread 4 that is being moved.

Figure 5:
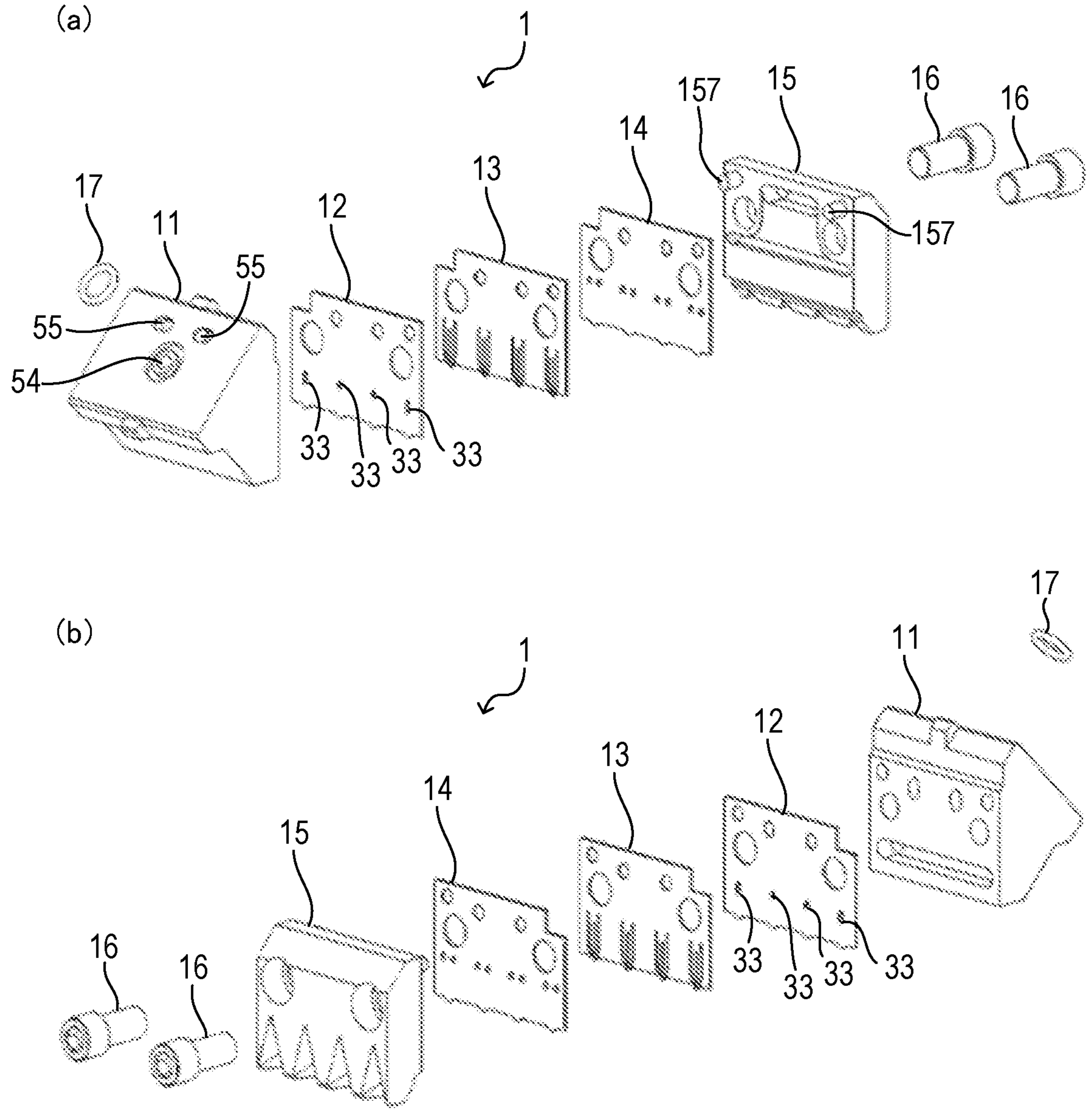
FIG. 5 is an exploded view of the nozzle.

FIG. 5 is an exploded view of the nozzle 1. The nozzle 1 includes a head body 11, an adhesive shim 12, a pattern shim 13, a gas shim 14, and a face plate 15. FIG. 5(*a*) is an exploded view of the nozzle 1 as viewed from the head body 11 side. FIG. 5(*b*) is an exploded view of the nozzle I as viewed from the face plate 15 side. The pattern shim 13 is sandwiched between a pair of side shims being the adhesive shim 12 and the gas shim 14. Three shims (the adhesive shim 12, the pattern shim 13, and the gas shim 14) are sandwiched between the head body 11 and the face plate 15, and are fixed all together with use of two screws (fixing means) 16. An O-ring 17 is configured to prevent leakage of the adhesive 5 through a space between the dispenser valve 60 and the nozzle 1.

Pattern Shim

Figure 6:
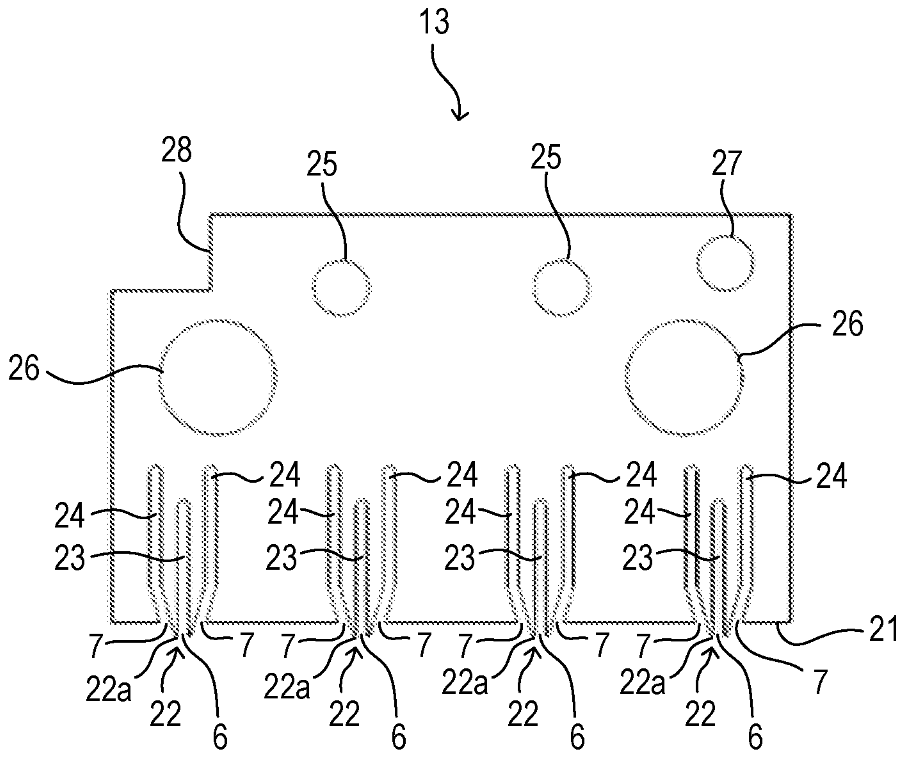
FIG. 6 is a view for illustrating a pattern shim.

FIG. 6 is a view for illustrating the pattern shim 13. The pattern shim 13 has a plurality of convex portions (first convex portions) 22, each having a tapered shape, which protrude outward from an outer edge 21. In this embodiment, the pattern shim 13 has four convex portions 22. Each of the convex portions 22 has a first slit (through groove) 23 formed therethrough. The first slit 23 is open at a tip 22*a* of the convex portion 22, and the opening of the first slit 23 functions as the adhesive ejection port 6. In this embodiment, the first slits 23 are arranged at predetermined intervals in the width direction B of the pattern shim 13. However, the first slits 23 are not required to be arranged at equal intervals. The pattern shim 13 has pairs of second slits (through grooves) 24. Each of the pairs of second slits 24 are open at positions on the outer edge 21, which are adjacent to a corresponding one of the convex portions 22. Each of pairs of second slits 24 are arranged bilaterally symmetric with respect to a corresponding one of the first slits 23. Open ends of the pair of second slits 24 function as the pair of gas discharge ports 7 being open at symmetric positions with respect to the adhesive ejection port 6.

The pattern shim 13 has a pair of gas holes (first gas holes) 25. The pattern shim 13 further has a pair of through holes 26, a positioning hole 27, and a positioning groove 28. The pair of through holes 26 allow passage of the two screws 16. The positioning hole 27 allows passage of one of a pair of positioning pins 157 provided to the face plate 15. The positioning groove 28 is engaged with another one of the pair of positioning pins 157. The positioning groove 28 is formed in such a manner as to define a part of an edge of the pattern shim 13. The positioning groove 28 is formed in a part of an outer periphery of the pattern shim 13, and thus is easily formed by wire discharge.

Adhesive Shim

Figure 7:
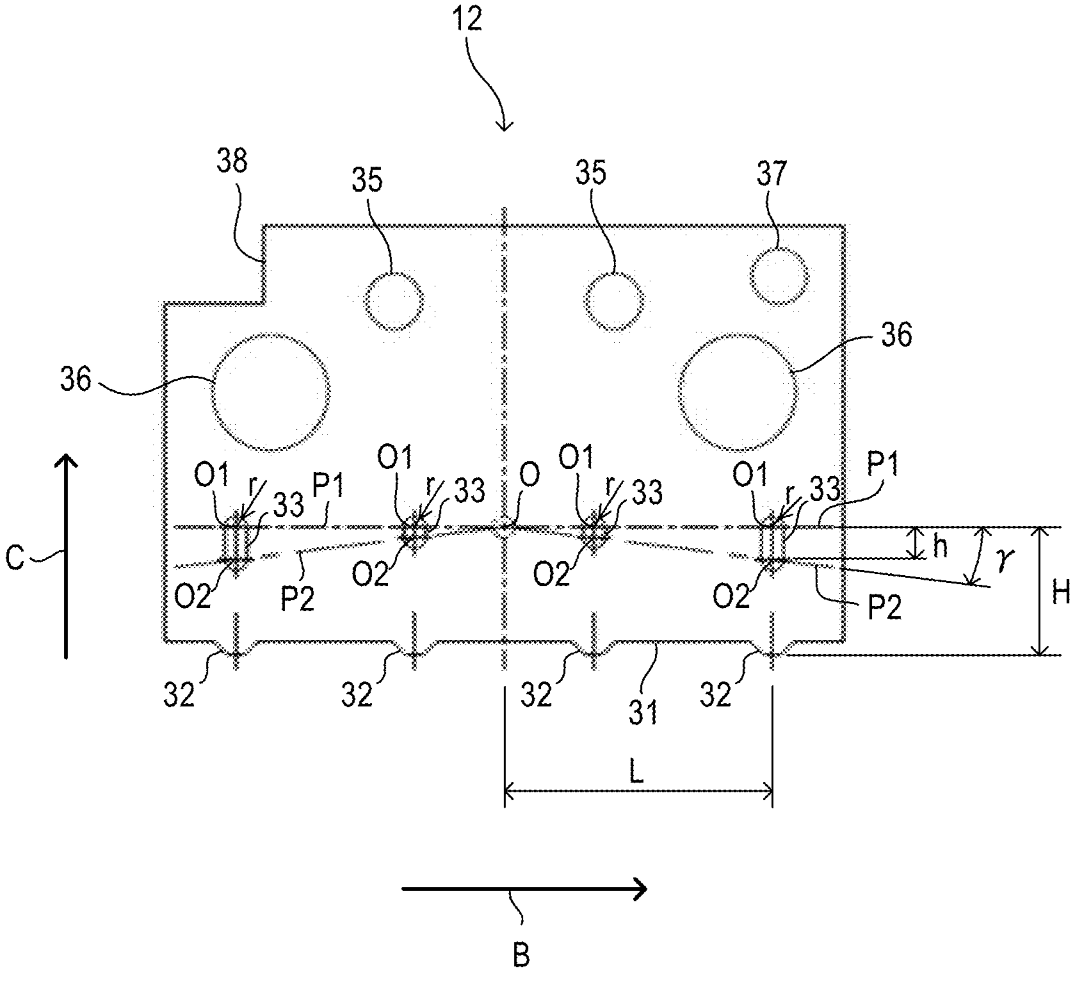
FIG. 7 is a view for illustrating an adhesive shim.

FIG. 7 is a view for illustrating the adhesive shim 12. The adhesive shim (hot melt shim) 12 serving as one of the side shims has a plurality of convex portions (second convex portions) 32, each having a tapered shape, which protrude outward from an outer periphery 31. In this embodiment, the adhesive shim 12 has four convex portions 32. Each of the convex portions 32 of the adhesive shim 12 has a shape wider than each of the convex portions 22 of the pattern shim 13. The adhesive shim 12 has a plurality of long holes (first holes) 33 serving as adhesive flow paths. In this embodiment, the plurality of long holes 33 are aligned with the plurality of convex portions 32, respectively, in a height direction C orthogonal to the moving direction A and the width direction B. Each of the long holes 33 may have a suitable shape such as a rectangular shape. In this embodiment, each of the long holes 33 have a vertically long shape with both end portions, each having a semi-circular shape.

A center O1 of an upper semi-circular shape of each of the long holes 33, which has a radius "r", is located at a distance H from a tip portion of a corresponding one of the convex portions 32. A line P1 passes through the centers O1 of the four long holes 33. A line P2 connects a center O of the adhesive shim 12 in the width direction B, which is located on the line P1, and centers O2 of lower semi-circular shapes of the long holes 33, each having the radius "r". The line P1 and the line P2 form a predetermined angle $\gamma$. A distance "h" between the center O1 of the upper semi-circular shape and the center O2 of the lower semi-circular shape of each of the long holes 33 is expressed by Expression 1 using the predetermined angle $\gamma$ and a distance L between the center O of the adhesive shim 12 in the width direction B and the corresponding long hole 33.

$$h=L\times\tan\gamma \qquad \text{Expression 1}$$

When L is equal to 0, the long hole 33 is a round-hole having the radius "r".

A length of each of the long holes 33 in the vicinity of end portions of the nozzle 1, which tend to eject a smaller amount of adhesive, is increased to shorten a length of a corresponding adhesive orifice. A pressure loss is reduced by shortening the length of each of the adhesive orifices. The ejection amounts from the plurality of adhesive ejection ports 6 can be made substantially equal regardless of positions of the adhesive ejection ports 6 in the width direction B. In this manner, a variation among the amounts of adhesive to be applied to a plurality of rubber threads 4 can be reduced.

The adhesive shim 12 has a pair of gas holes (second gas holes) 35. The adhesive shim 12 further has a pair of through holes 36, a positioning hole 37, and a positioning groove 38. The pair of through holes 36 allow passage of the two screws 16. The positioning hole 37 allows passage of one of the pair of positioning pins 157 provided to the face plate 15. The positioning groove 38 is engaged with another one of the pair of positioning pins 157. The positioning groove 38 is formed in such a manner as to define a part of an edge of the adhesive shim 12. The positioning groove 38 is formed in a part of an outer periphery of the adhesive shim 12, and thus is easily formed by wire discharge. When the adhesive shim 12 is superposed on the pattern shim 13, the long holes 33 communicate with the first slits 23, and the gas holes 35 communicate with the gas holes 25, respectively.

Gas Shim

Figure 8:
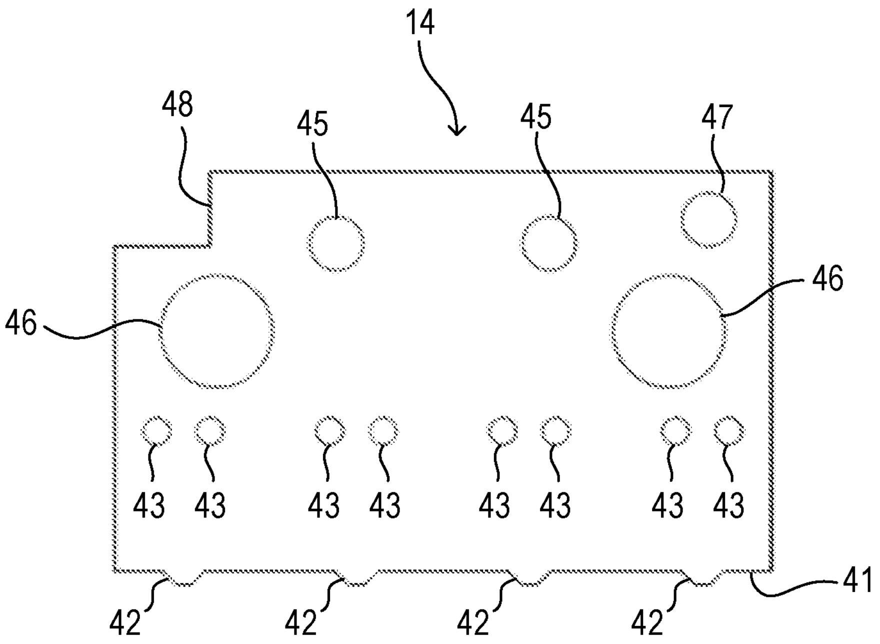
FIG. 8 is a view for illustrating a gas shim.

FIG. 8 is a view for illustrating the gas shim 14. The gas shim 14 serving as another one of the side shims has a plurality of convex portions (third convex portions) 42, each having a tapered shape, which protrude outward from an outer periphery 41. In this embodiment, the gas shim 14 has four convex portions 42. Each of the convex portions 42 of the gas shim 14 has a shape wider than each of the convex portions 22 of the pattern shim 13. The gas shim 14 has a plurality of gas holes (second holes) 43 serving as gas flow paths. In this embodiment, the gas shim 14 has eight gas holes 43. When the gas shim 14 is superposed on the pattern shim 13, the eight gas holes 43 communicate with the eight second slits 24 of the pattern shim 13, respectively.

The gas shim 14 has a pair of gas holes (third gas holes) 45. The gas shim 14 further has a pair of through holes 46, a positioning hole 47, and a positioning groove 48. The pair of through holes 46 allow passage of the two screws 16. The positioning hole 47 allows passage of the one of the pair of positioning pins 157 provided to the face plate 15. The positioning groove 48 is engaged with another one of the pair of positioning pins 157. The positioning groove 48 is formed in such a manner as to define a part of an edge of the gas shim 14. The positioning groove 48 is formed in a part of an outer periphery of the gas shim 14, and thus is easily formed by wire discharge. When the gas shim 14 is superposed on the pattern shim 13, the gas holes 45 communicate with the gas holes 25 of the pattern shim 13.

As illustrated in FIG. 3(*b*), the head body 11 has an inclined surface 50, which is inclined with respect to the moving direction A of the rubber threads 4. The adhesive shim 12, the pattern shim 13, and the gas shim 14 are laminated on the inclined surface 50 of the head body 11. The adhesive shim 12 is disposed in contact with the inclined surface 50. Axes of the first slits 23, which pass through the adhesive ejection ports 6, extend along the inclined surface 50 to form an acute angle with respect to the moving direction A of the rubber threads 4. Axes of the second slits 24, which pass through the gas discharge ports 7, extend along the inclined surface 50 to form an acute angle with respect to the moving direction A of the rubber threads 4. As illustrated in FIG. 4, the convex portion 22 of the pattern shim 13, the convex portion 32 of the adhesive shim 12, and the convex portion 42 of the gas shim 14 are superposed on one another to form the ejection port 2. When the pattern shim 13 having the first slits 23 and the second slits 24 is sandwiched between the adhesive shim 12 and the gas shim 14, the adhesive orifices and gas orifices are formed. The pattern shim 13 has a function as partition walls configured to define adhesive paths and gas paths formed in the nozzle 1. The convex portions 32 of the adhesive shim 12 and the convex portions 42 of the gas shim 14 also have a function of preventing accumulation of the adhesive at the ejection ports 2.

Head Body

Figure 9:
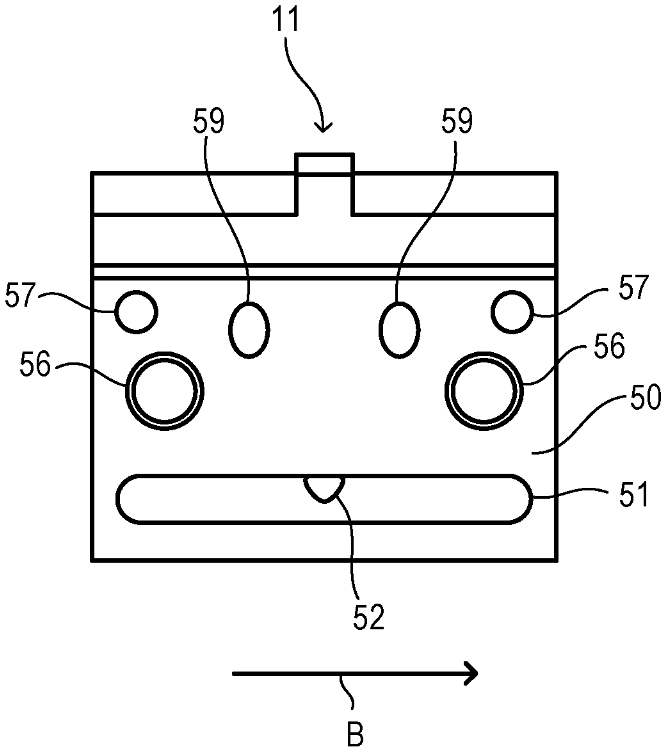
FIG. 9 is a view for illustrating a head body.

FIG. 9 is a view for illustrating the head body 11. An adhesive distribution groove 51, screw holes 56, positioning holes 57, and gas outlets 59 are formed in the inclined surface 50 of the head body 11. The screws 16 are threadedly engaged with the screw holes 56, respectively. The positioning holes 57 are engaged with the positioning pins 157, respectively. The adhesive distribution groove 51 is an elongated horizontal groove extending in the width direction B of the nozzle 1. The head body 11 further has an adhesive inlet 54 and a pair of gas inlets 55 (FIG. 5(A)).

Figure 10:
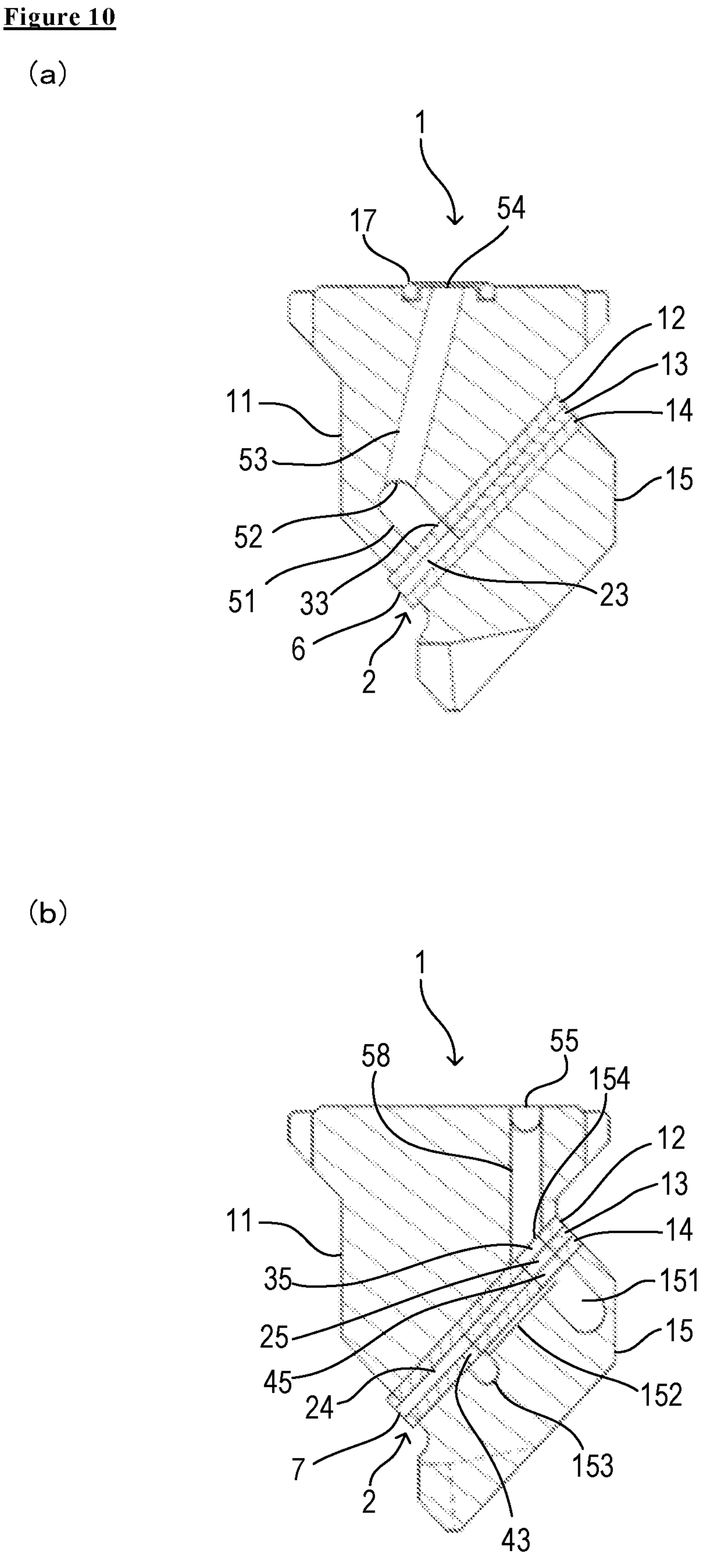
FIG. 10 is a sectional view of the nozzle.

FIG. 10 is a sectional view of the nozzle 1. The head body 11 has an adhesive flow path 53 and a pair of gas flow paths 58. FIG. 10(*a*) is a sectional view of the nozzle 1, which is taken along a plane containing an axis of the adhesive flow path 53. The adhesive flow path 53 communicates with the adhesive inlet 54 formed in a top surface of the head body 11. When the nozzle 1 is mounted to the dispenser valve 60, the adhesive inlet 54 communicates with the adhesive discharge passage 97 of the dispenser valve 60. An adhesive outlet 52 of the adhesive flow path 53 communicates with the adhesive distribution groove 51.

The adhesive distribution groove 51 communicates with the plurality of long holes 33 formed in the adhesive shim 12. The long holes 33 communicate with the first slits 23 formed in the pattern shim 13, respectively. The adhesive discharged from the adhesive discharge passage 97 of the dispenser valve 60 passes through the adhesive inlet 54, the adhesive flow path 53, the adhesive outlet 52, the long holes 33, and the first slits 23 to be ejected from the adhesive ejection ports 6 of the ejection ports 2.

Face Plate

Figure 11:
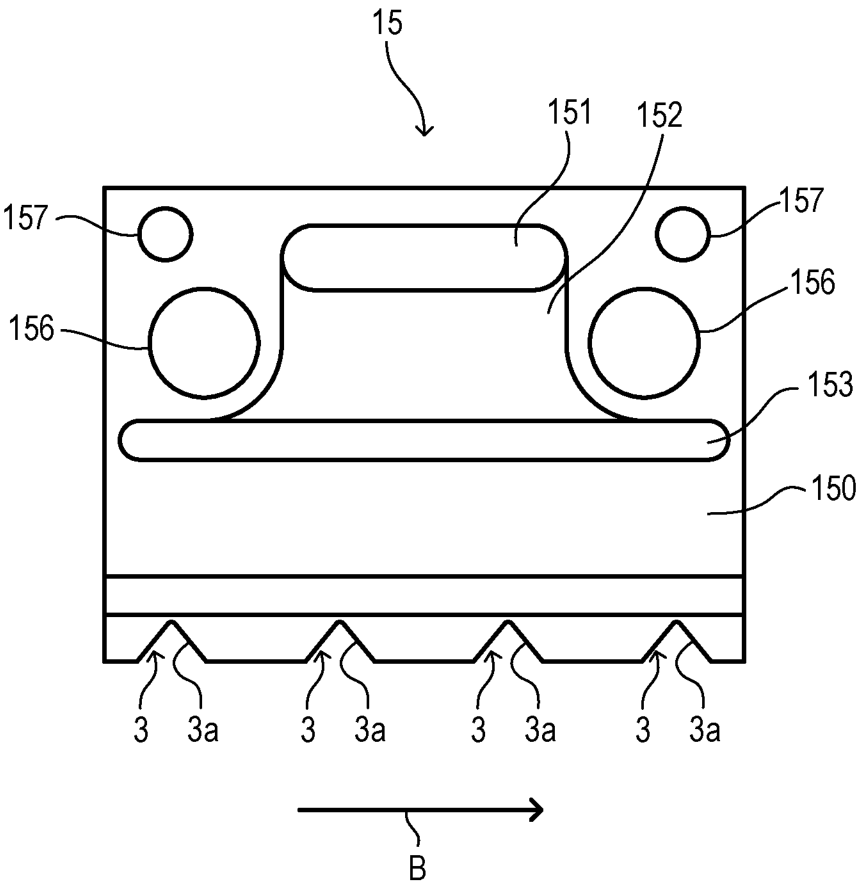
FIG. 11 is a view for illustrating a face plate.

FIG. 11 is a view for illustrating the face plate 15. A mount surface 150 of the face plate 15 has a first gas distribution groove 151, a second gas distribution groove 152, a third gas distribution groove 153, a pair of through holes 156, and a pair of positioning pins 157. The pair of through holes 156 allow passage of the two screws 16. The face plate 15 further has the four guide grooves 3. A length of the third gas distribution groove 153 is longer than a length of the first gas distribution groove 151 in the width direction B. The second gas distribution groove 152, which brings the first gas distribution groove 151 and the third gas distribution groove 153 into communication with each other, has such an inverted V shape that widens toward a lower end so as to spread a gas in the width direction B while the gas is flowing from the first gas distribution groove 151 into the third gas distribution groove 153.

FIG. 10(*b*) is a sectional view of the nozzle 1, which is taken along a plane containing an axis of one of the gas flow paths 58. The gas flow paths 58 communicate with the gas inlets 55 formed in the top surface of the head body 11, respectively. When the nozzle 1 is mounted to the dispenser valve 60, the pair of gas inlets 55 communicate with the pair of gas discharge flow passages 98 of the dispenser valve 60, respectively. Gas outlets 154 of the pair of gas flow paths 58 communicate with the pair of gas holes 35 of the adhesive shim 12, respectively.

When the face plate 15 is mounted to the head body 11 with use of the screws 16 while the gas shim 14, the pattern shim 13, and the adhesive shim 12 are sandwiched therebetween, the first gas distribution groove 151 of the face plate 15 communicates with the pair of gas holes 45 of the gas shim 14, and the third gas distribution groove 153 communicates with the eight gas holes 43. The gas discharged through the gas discharge passages 98 of the dispenser valve 60 passes through the gas inlets 55, the gas flow paths 58, the gas outlets 154, the gas holes 35, the gas holes 25, the gas holes 45, the first gas distribution groove 151, the second gas distribution groove 152, the third gas distribution groove 153, the gas holes 43, and the second slits 24 to be jetted from the gas discharge ports 7 of the ejection ports 2.

Discharge Angle of Adhesive

As illustrated in FIG. 3(*b*), the head body 11 has the inclined surface 50 that forms an acute angle with respect to the moving direction A of the rubber threads 4. The adhesive shim 12, the pattern shim 13, and the gas shim 14 are superposed on the inclined surface 50 to form the ejection ports 2. When the adhesive 5 is ejected, and the gas is jetted from the ejection ports 2, the adhesive 5 can be applied in a wave pattern at the acute angle with respect to the moving direction A of the rubber threads 4. An ejection direction of the adhesive 5 is inclined with respect to the moving direction A of the rubber threads 4, and thus the ejected adhesive 5 gently comes into contact with each of the rubber threads 4. Accordingly, the adhesive 5 is less liable to be repelled by the rubber threads 4.

Further, a relative speed between the ejected adhesive 5 and each of the rubber threads 4 is reduced by a component (=cos θ) of an ejection speed vector of the adhesive 5 in the moving direction A of the rubber threads 4. Thus, repelling and scattering of the adhesive 5 by the rubber threads 4 can be suppressed even under a condition where the moving speed of the rubber threads 4 is higher in comparison to a case in which the adhesive 5 is applied at a substantially right angle with respect to the moving direction A. The adhesive 5 is more likely to adhere to the rubber threads 4 even under a condition where the adhesive 5 is liable to be repelled by the rubber threads 4, for example, in a case in which the adhesive 5 has a low viscosity or a case in which the ejection amount of the adhesive 5 is small, specifically, the ejection speed of the adhesive 5 is low, in comparison to a case in which the adhesive 5 is applied at a substantially right angle with respect to the moving direction A of the rubber threads 4. Thus, the adhesive 5 can be stably applied under a wider range of conditions than a range of conditions in the related art.

In this embodiment, as illustrated in FIG. 3(*b*), an ejection angle θ of the adhesive 5 with respect to the moving direction A of the rubber threads 4 is set to 45 degrees. When the ejection angle θ is larger than 45 degrees, the relative speed between the adhesive 5 and the rubber threads 4 is increased. Thus, when the ejection angle θ is larger than 45 degrees, the scattering of the adhesive 5 cannot be suppressed in some cases under a condition in which the moving speed of the rubber threads 4 is higher.

On the contrary, when the ejection angle θ is smaller than 45 degrees, the relative speed between the adhesive 5 and the rubber threads 4 is decreased. Further, an application position (contact position) AP of the adhesive 5 to each of the rubber threads 4 is located farther from a corresponding one of the ejection ports 2. An oscillation width of the adhesive 5 that is oscillated in a wave pattern increases as a distance of the application position AP of the adhesive 5 from the corresponding ejection port 2 increases. When the oscillation width of the adhesive 5 is increased, the adhesive 5 is further stretched and narrowed to result in a smaller fiber diameter of the adhesive 5. Fibers of the adhesive 5, which each have a small fiber diameter, shake widely in a fore-and-aft direction (moving direction A) due to disturbance (mainly, an air flow generated by transport of the first substrate 8 and the second substrate 9). Thus, the fiber diameter and wave pattern intervals of the adhesive 5 applied to each of the rubber threads 4 become irregular to result in an unstable application state. As the ejection angle θ is decreased, application stability is more impaired. Thus, it is desired that the ejection angle θ be equal to or larger than about 20 degrees.

In this embodiment, the adhesive 5 is ejected at an acute angle with respect to the moving direction A of the rubber threads 4. As a result, stable application is enabled under a wide range of conditions including, for example, a case in which a production line is conducted at a high speed, a case in which an application amount is small, and a case in which the adhesive has a low viscosity. As described above, it is important for application stability that the ejection angle θ, and in turn, the application position AP are kept constant. In this embodiment, the face plate 15 has the guide grooves 3 configured to guide the rubber threads 4. The guide grooves 3 are located in the vicinity of the ejection ports 2, respectively. Each of the guide grooves 3 has a concave surface 3*a* configured to receive a corresponding one of the rubber threads 4 and guide the corresponding rubber thread 4 along the moving direction A. Each of the guide grooves 3 suppresses waviness of the corresponding rubber thread 4 until just before the application of the adhesive 5 is started, and guides the corresponding rubber thread 4 to the appropriate application position AP.

The nozzle 1 has the guide grooves 3 having a guiding function, and hence a positional relationship between each of the ejection ports 2 and a corresponding one of the rubber threads 4 can be kept constant. Thus, shaking of the rubber threads 4 is suppressed to a position immediately proximal to the application position AP only by inserting the rubber threads 4 into the guide grooves 3 in such a manner that the rubber threads 4 are in contact with the guide grooves 3, respectively. Further, each of the guide grooves 3 enables the ejection angle θ formed by the ejection direction of the adhesive 5 with respect to the moving direction A of the rubber threads 4 to be maintained at a given angle. The nozzle 1 itself has a guiding function for the rubber threads 4. Thus, the adhesive 5 ejected at the acute angle with respect to the rubber threads 4 is reliably applied on each of the rubber threads 4. A guide roller configured to guide the rubber threads 4 may be provided in the vicinity of the nozzle 1. In this case, however, a positional relationship between the nozzle 1 and the guide roller is required to be subjected to fine adjustment so that each of the rubber threads 4 passes through the optimal application position AP.

When fibers of the oscillated adhesive 5 are to be applied to a plurality of rubber threads 4, it is preferred that ejection amounts of the adhesive 5 to be ejected from the ejection ports 2, amplitudes and amplitude cycles (frequencies) of the wave patterns of the adhesive streams be set uniform over all the ejection ports 2. In this manner, the fibers of the adhesive 5, which have the same fiber diameter, come into contact with the rubber threads 4 in the same cycles. As a result, an ideal application state without a difference in bonding strength among the rubber threads 4 can be obtained. To achieve the ideal application state, flow rates of the adhesive streams ejected from and flow rates of gas streams jetted from the plurality of ejection ports 2 are required to be set equal. In this embodiment, the structure for achieving a uniform flow-rate balance among the ejection ports 2 is provided in flow paths for the adhesive 5 and flow paths for the gas to thereby enable uniform and stable application.

Distribution of Adhesive

The adhesive 5 flows from the adhesive inlet 54 of the nozzle 1, which is illustrated in FIG. 10(*a*), through the adhesive flow path 53 into the adhesive distribution groove 51 illustrated in FIG. 9. The adhesive 5 is distributed in the width direction B of the nozzle 1 through the adhesive distribution groove 51. The adhesive outlet 52 of the adhesive flow path 53 is located in a center of the adhesive distribution groove 51 in the width direction B. Thus, a flow rate of the adhesive 5 tends to be larger in the center of the adhesive distribution groove 51, and tends to be smaller at both end portions of the adhesive distribution groove 51 in the width direction B. To adjust a non-uniform distribution of the adhesive 5 flowing through the adhesive distribution groove 51 so as to achieve more uniform distribution, the adhesive shim 12 has the plurality of long holes (elongated groove holes) 33 including those having longer lengths in the center than lengths of those in the end portions, as illustrated in FIG. 7. Each of the plurality of long holes 33 has a longer length along a direction in which the first slits 23 extend. The distribution of the adhesive 5 is uniformized by adjusting the lengths of the plurality of long holes 33 in a longitudinal direction in accordance with distances from the adhesive outlet 52. In this embodiment, the flow rate balance of the adhesive 5 among the adhesive ejection ports 6 is adjusted by changing the lengths of the long holes 33 in accordance with the distance L from the center O of the adhesive shim 12 to the long hole 33. As a result, the ejection amounts of the adhesive 5 can be set substantially equal to each other for the adhesive ejection ports 6.

Figure 12:
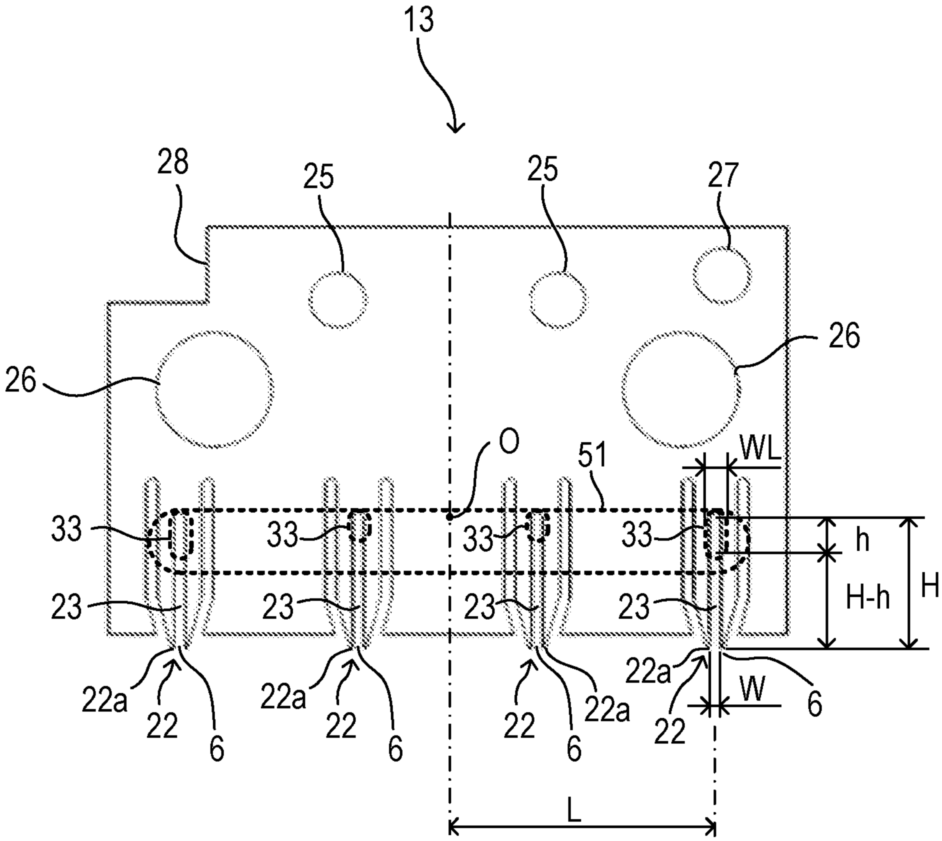
FIG. 12 is an explanatory view for illustrating a positional relationship among an adhesive distribution groove, first slits, and long holes.

FIG. 12 is an explanatory view for illustrating a positional relationship among the adhesive distribution groove 51, the first slits 23, and the long holes 33. Positions of tips of the convex portions 32 of the adhesive shim 12, positions of the tips 22*a* of the convex portions 22 of the pattern shim 13, and positions of tips of the convex portions 42 of the gas shim 14 are aligned with each other. A width W of each of the tips 22*a* of the convex portions 22 of the pattern shim 13 is the same as a width of each of the tips of the convex portions 32 of the adhesive shim 12 and a width of each of the tips of the convex portions 42 of the gas shim 14. A length H-h of each of the adhesive orifices, which is determined by a corresponding one of the long holes 33 of the adhesive shim 12 and a corresponding one of the first slits 23 of the pattern shim 13, is expressed by Expression 2.

$$H-h=H-L\times\tan\gamma \qquad \text{Expression 2}$$

As is understood from Expression 2, the length H-h of the adhesive orifice becomes shorter as a distance of the first slit 23 from the center O of the pattern shim 13 increases. When the length H-h of the adhesive orifice becomes shorter, resistance against flow of the adhesive 5 is reduced. Thus, the adhesive 5 is allowed to easily flow. In this manner, the flow rates of the streams of the adhesive flowing from the adhesive distribution groove 51 through the long holes 33 and the first slits 23 into the adhesive ejection ports 6 can be made equal to each other. Widths of the first slits 23 can be suitably set in accordance with conditions of use such as the viscosity or the ejection amount of the adhesive 5. A width WL of each of the long holes 33 is larger than the width W of each of the first slits 23. In this embodiment, the width WL of each of the long holes 33 is substantially twice as large as the width W of each of the first slits 23. However, the width WL of each of the long holes 33 is not limited to the above-mentioned value in the present invention. The width WL of each of the long holes 33 may be set to fall within a range of from 1.2 times to three times as large as the width W of each of the first slits 23. The width WL of each of the long holes 33 may be more than three times the width W of each of the first slits 23.

As means for adjusting the flow rates of the adhesive streams among the adhesive orifices, the adhesive shim 12 may have round-holes (first holes) having different diameters in place of the long holes 33 having different lengths. The round-holes having different diameters can produce the same effects as those obtained by the long holes 33 having different lengths. The pressure loss is proportional to a square of a flow path diameter. Thus, differences in diameter of the round-holes are extremely small among the adhesive orifices. Thus, the round-holes are required to be formed with high accuracy.

Figure 13:
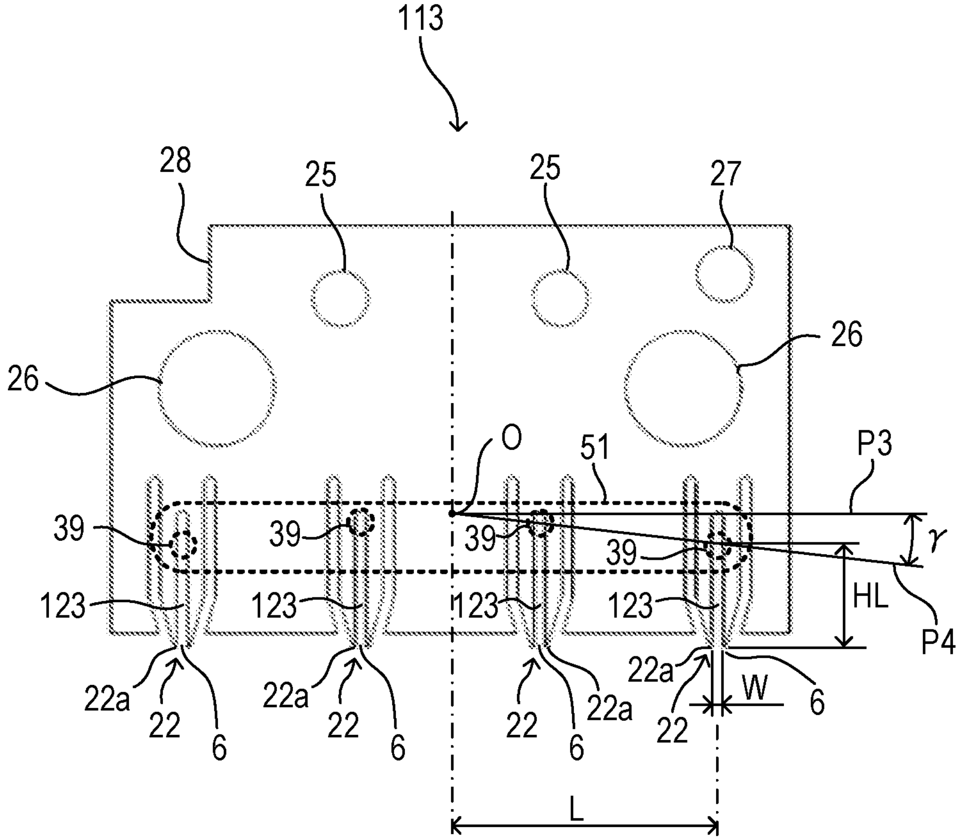
FIG. 13 is an explanatory view for illustrating a positional relationship among the adhesive distribution groove, the first slits, and round-holes in a modification example.

Further, another means for adjusting the flow rates of the adhesive streams among the adhesive orifices is illustrated in FIG. 13. In a modification example of the adhesive shim 12, a plurality of round-holes (first holes) 39 having the same diameter are formed at positions having different distances from the corresponding convex portions 32 in place of the plurality of long holes 33. FIG. 13 is an explanatory view for illustrating a positional relationship among the adhesive distribution groove 51, first slits 123, and the round-holes 39 in the modification example. A line P3 extends along the width direction B of the adhesive shim 12. A line P4 connects a center O of the adhesive shim 12 in the width direction B, which is located on the line P3, and centers of the round-holes 39. The line P3 and the line P4 form a predetermined angle γ. Each of the round-holes 39 is located at an intersection between the line P4 that forms the predetermined angle γ with respect to the line P3 extending along the width direction B of the adhesive shim 12 and an axis of a corresponding one of the first slits 123. A pattern shim 113 has the first slits 123, each having a length HL that is set in accordance with a distance of a corresponding one of the round-holes 39 from a corresponding one of the convex portions 32. In the modification example illustrated in FIG. 13, the length HL of the adhesive orifice changes in accordance with the distance L from the center O of the pattern shim 113 to the first slit 123. In this manner, the same effects can be obtained. In this case, both of the positions of the round-holes 39 of the adhesive shim 12 and the lengths of the first slits 123 of the pattern shim 113 are required to be changed.

A diameter of each of the round-holes 39 is larger than the width W of each of the first slits 123. In this embodiment, the diameter of each of the round-holes 39 is substantially twice as large as the width W of each of the first slits 123. However, the diameter of each of the round-holes 39 is not limited to the above-mentioned value in the present invention. The diameter of each of the round-holes 39 may be set to fall within a range of 1.2 times to three times as large as the width W of each of the first slits 123. The diameter of each of the round-holes 39 may be more than three times the width W of each of the first slits 123.

Distribution of Gas

Figure 14:
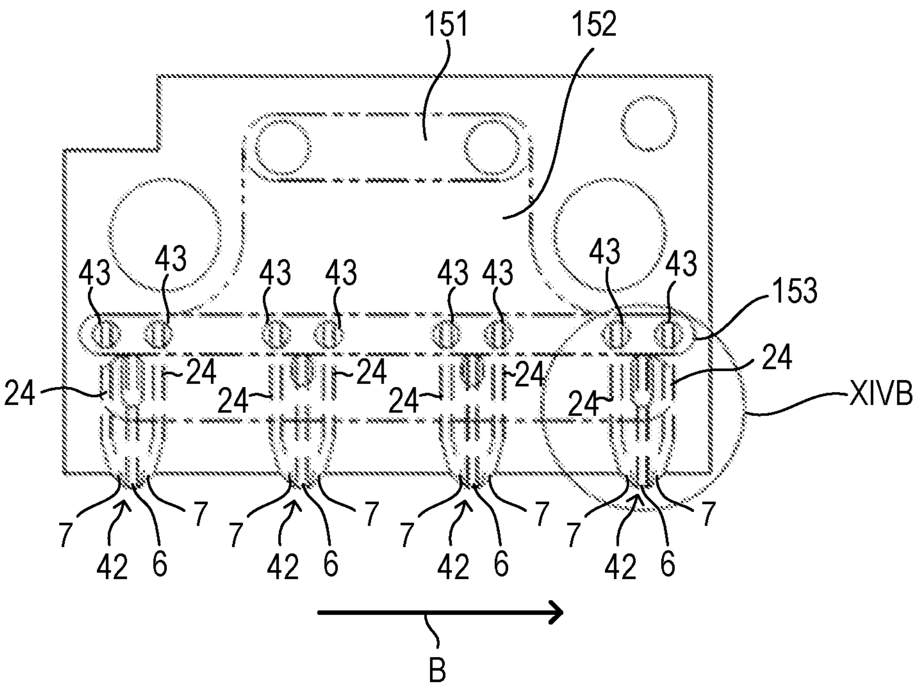
FIG. 14 is an explanatory view for illustrating a positional relationship among gas distribution grooves, second slits, and gas holes.
Figure 14:
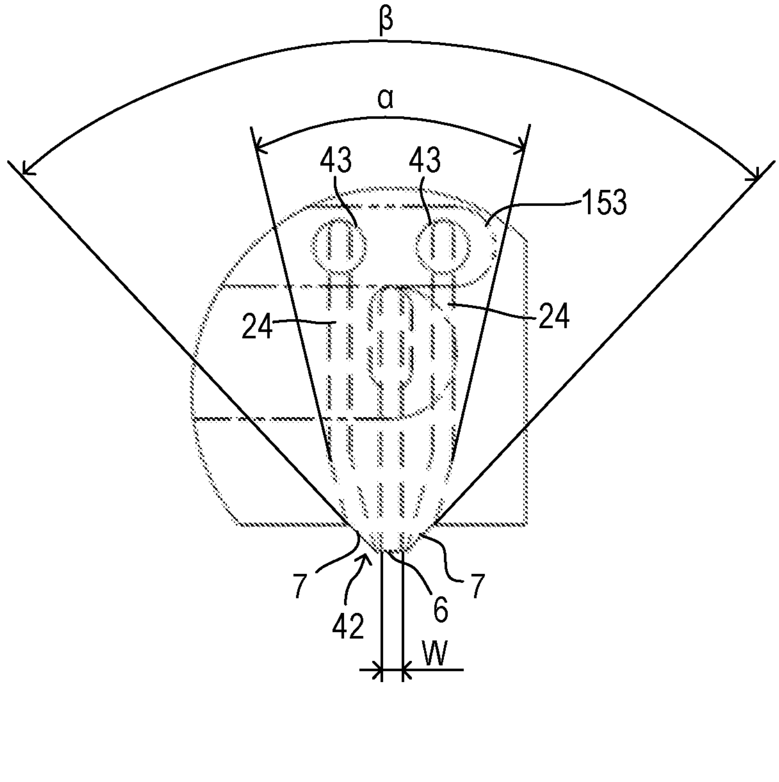

As illustrated in FIG. 10(*b*), the first gas distribution groove 151 is required to have a larger depth than those of the second gas distribution groove 152 and the third gas distribution groove 153 so as to serve as a buffer configured to increase a volume of the gas. The first gas distribution groove 151 has an action to join gas streams flowing from the two gas flow paths 58 and accumulate the gas. FIG. 14 is an explanatory view for illustrating a positional relationship among the first gas distribution groove 151, the second gas distribution groove 152, the third gas distribution groove 153, the second slits 24, and the gas holes 43. As illustrated in FIG. 14(*a*), the second gas distribution groove 152 gradually spreads the gas, which has been accumulated in the first gas distribution groove 151, in the width direction B into a thin layer, and evenly diffuses the gas in the width direction B. The second gas distribution groove 152 is a shallow groove for providing resistance to the gas to spread the gas so that a larger amount of gas does not flow in the center of the second gas distribution groove 152.

The third gas distribution groove 153 has a larger depth than that of the second gas distribution groove 152. The third gas distribution groove 153 is configured to receive the spread gas to feed the gas into the eight gas holes 43 of the gas shim 14. In this manner, the gas is evenly spread in the width direction B of the nozzle 1. The gas that is evenly diffused in the width direction passes through the eight gas holes 43, and is distributed to the eight second slits 24. In this manner, the gas is distributed through three stages with the first gas distribution groove 151, the second gas distribution groove 152, and the third gas distribution groove 153 of the face plate 15. Through the three-stage distribution, ejection amounts of gas jetted from the eight gas discharge ports 7 can be made substantially equal to each other.

In this embodiment, the face plate 15 has the first gas distribution groove 151, the second gas distribution groove 152, and the third gas distribution groove 153. However, the first gas distribution groove 151, the second gas distribution groove 152, and the third gas distribution groove 153 are not required to be formed in the face plate 15. For example, similar gas distribution grooves may be formed by additionally providing a plurality of shims, each having through grooves. When the gas is caused to pass through the gas distribution grooves formed in the plurality of laminated shims, the same effects are obtained.

FIG. 14(*b*) is an enlarged view of a portion XIVB surrounded by a circle in FIG. 14(*a*). As illustrated in FIG. 14(*b*), the second slits 24 are arranged bilaterally symmetric with respect to the first slit 23 so as to impinge the gas streams on the adhesive stream ejected from the adhesive ejection port 6 in a symmetric manner from right and left sides. The second slits 24 are inclined with respect to the first slit 23 in the vicinity of the gas discharge ports 7. The gas streams are symmetrically discharged from the pair of gas discharge ports 7 toward the adhesive stream ejected from the adhesive ejection port 6 in such a manner that the gas streams discharged from the pair of gas discharge ports 7 travel over the same distance from the adhesive ejection port 6 to impinge on the adhesive stream ejected from the adhesive ejection port 6. The oscillation width of the wave pattern of the adhesive 5 can be changed by changing a discharge angle α between the gas streams from the pair of gas discharge ports 7. When the discharge angle α is increased, the oscillation width of the wave pattern can be increased. On the contrary, when the discharge angle α is reduced, the oscillation width of the wave pattern can be reduced. Further, when a discharge pressure (discharge amount) of the gas is increased, the oscillation width of the wave pattern of the adhesive 5 can also be increased.

Figure 15:
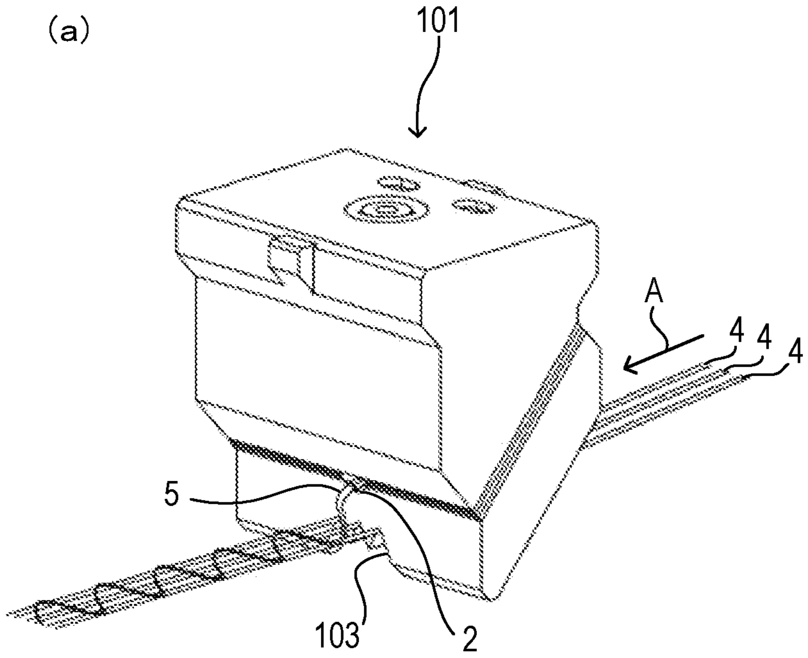
FIG. 15 is a view for illustrating a nozzle configured to apply a single fiber of adhesive to a plurality of rubber threads.
Figure 15:
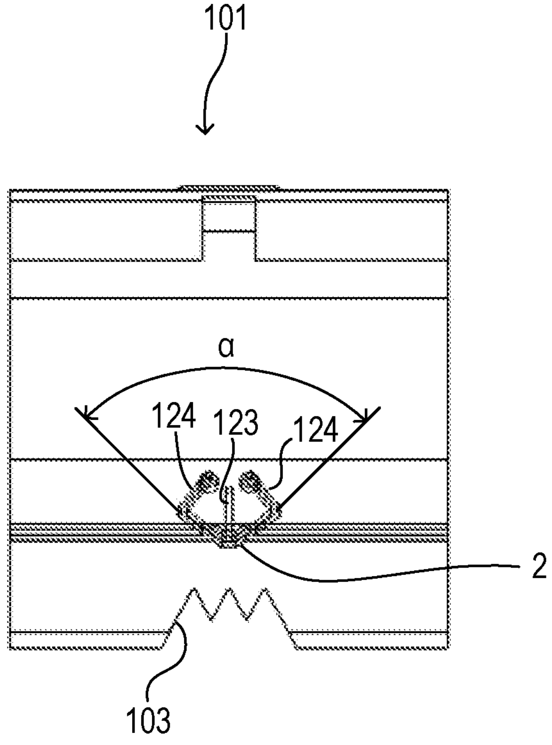

FIG. 15 is a view for illustrating a nozzle 101 configured to apply a single fiber of the adhesive 5 ejected from the one ejection port 2 to the plurality of rubber threads 4. A plurality of guide grooves 103 are formed for one ejection port 2. The nozzle 101 has a pair of second slits 124 for forming gas orifices, which are inclined at a large angle with respect to the first slit 123 for forming an adhesive orifice. As illustrated in FIG. 15, when the fibers of the adhesive 5 ejected from the single ejection port 2 are to be applied on the plurality of rubber threads 4, it is effective to increase the discharge angle α formed between the gas streams.

When viewed along the moving direction A of the rubber threads 4, the convex portions 42 of the gas shim 14 and the convex portions 32 of the adhesive shim 12 are disposed in such a manner as to cover the gas discharge port 7. As illustrated in FIG. 14(*b*), a convex-portion angle β of the convex portion 42 of the gas shim 14 and the convex portion 32 of the adhesive shim 12 is set larger than the discharge angle α formed between the gas streams. As a result, even when the pattern shim 13 is replaced later by a pattern shim having a larger discharge angle α between the gas streams, both sides of the pair of gas discharge ports 7 of the new pattern shim 13 are covered with the convex portion 42 of the gas shim 14 and the convex portion 32 of the adhesive shim 12 to thereby ensure a sufficient sealing property. When the convex-portion angle ß is smaller than the discharge angle α (β<α), part of each of the gas discharge ports 7 formed in the pattern shim 13 protrudes from the adhesive shim 12 and the gas shim 14. As a result, both sides of each of the gas ejection ports 7 cannot be sufficiently covered. In this case, the gas is discharged unstably. Further, the sealing property is insufficient, and thus the adhesive 5 may leak from a space between the shims. Thus, the convex-portion angle β is set equal to or larger than the discharge angle α.

According to this embodiment, the adhesive 5 can be stably applied by evenly determining the application patterns of the adhesive streams from the adhesive ejection ports 6 and the discharge patterns of the gas streams from the gas ejection ports 7.

According to this embodiment, uniformity in the distribution of the adhesive to be distributed to the plurality of adhesive ejection ports 6 and uniformity in the distribution of the gas to be distributed to the plurality of gas discharge ports 7 can be improved.

The present invention is not limited to the above-mentioned embodiment and can be embodied in a variety of other modes without departing from a characteristic matter of the present invention. Hence, the above-mentioned embodiment is merely given as an example and should not be exclusively construed. The scope of the present invention is not restricted to this specification at all and is only defined by the scope of claims. Further, all modifications and changes within the scope of claims and its equivalent fall within the scope of the present invention.

LIST OF PARTS AND REFERENCE NUMERALS

1 . . . nozzle
6 . . . adhesive ejection port
7 . . . gas discharge port
11 . . . head body
12 . . . adhesive shim
13 . . . pattern shim
14 . . . gas shim
15 . . . face plate
16 . . . screw (fixing means)
22 . . . convex portion (first convex portion)
23 . . . first slit
24 . . . second slit
25 . . . gas hole (first gas hole)
32 . . . convex portion (second convex portion)
33, 39 . . . long hole (first hole)
35 . . . gas hole (second gas hole)
42 . . . convex portion (third convex portion)
43 . . . gas hole (second hole)
45 . . . gas hole (third gas hole)
51 . . . adhesive distribution groove
52 . . . adhesive outlet
53 . . . adhesive flow path
54 . . . adhesive inlet
55 . . . gas inlet
58 . . . gas flow path
59 . . . gas outlet
151 . . . first gas distribution groove
152 . . . second gas distribution groove
153 . . . third gas distribution groove

What is claimed is:

1. A method of making a disposable hygiene product, the method comprising:
- moving a plurality of rubber threads;
- depressurizing a first gas using a first regulator;
- supplying the first gas depressurized by the first regulator, using a solenoid valve, in accordance with an external signal to open and close an adhesive discharge port using a dispenser valve;
- applying a plurality of hot melt adhesive fibers discharged from a nozzle on the plurality of rubber threads, respectively, in a wave pattern formed by impinging a second gas on the plurality of hot melt adhesive fibers; and
- sandwiching the plurality of rubber threads on which the plurality of hot melt adhesive fibers are applied, respectively, by a first substrate and a second substrate.

2. The method of claim 1, wherein the disposable hygiene product comprises a diaper.

3. The method of claim 1, further comprising:

storing a hot melt adhesive in a tank inside a melter; and pumping, using a pump, the hot melt adhesive from the melter through a heating hose to a manifold.

4. The method of claim 3, further comprising receiving, at the melter, a speed signal corresponding to a moving speed of the plurality of rubber threads from a base unit.

5. The method of claim 4, further comprising controlling an amount of the hot melt adhesive supplied by the pump in accordance with the speed signal.

6. The method of claim 5, further comprising increasing the amount of the hot melt adhesive supplied by the pump in response to an increase of the speed signal.

7. The method of claim 5, further comprising decreasing the amount of the hot melt adhesive supplied by the pump in response to a decrease of the speed signal.

8. The method of claim 1, further comprising:

depressurizing the second gas using a second regulator; and impinging, using the nozzle, the second gas depressurized by the second regulator on the plurality of hot melt adhesive fibers.

9. The method of claim 1, further comprising intermittently opening and closing the adhesive discharge port to intermittently apply the plurality of hot melt adhesive fibers discharged from the nozzle on the plurality of rubber threads.

10. The method of claim 8, further comprising continuously supplying the second gas depressurized by the second regulator to the nozzle and impinging the second gas on the plurality of hot melt adhesive fibers.

11. The method of claim 8, further comprising controlling the second regulator in accordance with an electric signal corresponding to a moving speed of the plurality of rubber threads.

12. The method of claim 11, further comprising adjusting a width of oscillation of the hot melt adhesive fibers discharged from the nozzle by regulating a pressure of the second gas.

13. The method of claim 1, further comprising applying the plurality of hot melt adhesive fibers discharged from the nozzle on an outer periphery of the plurality of rubber threads.

14. The method of claim 1, wherein the plurality of rubber threads are wound into a roll, the method further comprising:

supplying the plurality of rubber threads from the roll to the nozzle via a guide roller.

15. The method of claim 1, wherein the first substrate is wound into a first roll, the method further comprising:

supplying the first substrate from the first roll to a first transport roller to be bonded with the plurality of rubber threads applied with the plurality of hot melt adhesive fibers.

16. The method of claim 15, wherein the second substrate is wound into a second roll, the method further comprising:

supplying the second substrate from the second roll to a second transport roller to be bonded with the plurality of rubber threads applied with the plurality of hot melt adhesive fibers.

17. The method of claim 1, wherein the nozzle comprises:

a pattern shim having a plurality of tapered first convex portions protruding from an outer edge outwardly;

an adhesive shim having a plurality of tapered second convex portions protruding from an outer edge outwardly and having a shape wider than the plurality of tapered first convex portions;

a gas shim having a plurality of tapered third convex portions protruding from an outer edge outwardly and having a shape wider than the plurality of tapered first convex portions;

a head body having an adhesive inlet, an adhesive outlet, and an adhesive flow path connecting the adhesive inlet and the adhesive outlet;

a face plate having a first gas distribution groove, a second gas distribution groove communicating with the first gas distribution groove, and a third gas distribution groove communicating with the second gas distribution groove; and a fixing means for fixing the head body, the adhesive shim, the pattern shim, the gas shim, and the face plate arranged in order of mention, wherein the plurality of tapered first convex portions are sandwiched by the plurality of tapered second convex portions and the plurality of tapered third convex portions to form adhesive discharge ports and to form gas discharge ports provided on both sides of each of the adhesive discharge ports, wherein an adhesive discharged from the adhesive discharge ports is configured to be applied on objects moving in a moving direction with respect to the adhesive discharge ports, and wherein the head body has an inclined surface that is inclined so as to form an acute angle with respect to the moving direction, the adhesive shim is disposed in contact with the inclined surface, and the pattern shim, the adhesive shim, and the gas shim are superposed on the inclined surface to form the adhesive discharge ports and the gas discharge ports.

18. The method of claim 17, wherein:

the pattern shim further comprises a plurality of first slits which open at tips of the plurality of tapered first convex portions, respectively, a plurality of second slits provided on both sides of each of the plurality of first slits and open at portions adjacent to a corresponding first convex portion, and a first gas hole;

the adhesive shim further comprises a plurality of first holes as adhesive flow paths and a second gas hole;

the gas shim further comprises a plurality of second holes as gas flow paths and a third gas hole; and the head body further comprises an adhesive distribution groove communicating with the adhesive outlet, a gas inlet, a gas outlet, and a gas flow path connecting the gas inlet and the gas outlet, wherein the fixing means is configured to fix the head body, the adhesive shim, the pattern shim, the gas shim, and the face plate arranged in order of mention so that the adhesive distribution groove communicates with the plurality of first holes, the plurality of first holes communicate with the plurality of first slits, the gas outlet communicates with the first gas hole, the first gas hole communicates with the second gas hole, the second gas hole communicates with the third gas hole, the third gas hole communicates with the first gas distribution groove, the third gas distribution groove communicates with the plurality of second holes, and the plurality of second holes communicates with the plurality of second slits, wherein the adhesive discharge ports are formed at openings of the plurality of first slits and the gas discharge ports are formed at openings of the plurality of second slits, and wherein the plurality of first holes are configured so that a distance from an adhesive discharge port becomes shorter as a distance from the adhesive outlet becomes longer.

19. The method of claim 18, wherein:

the adhesive distribution groove and the gas outlet are formed in the inclined surface;

axes passing through the adhesive discharge ports of the plurality of first slits extend along the inclined surface to form an acute angle with respect to the moving direction; and axes passing through the gas discharge ports of the plurality of second slits extend along the inclined surface to form an acute angle with respect to the moving direction.

* * * * *